(12) United States Patent
Malanson et al.

(10) Patent No.: US 9,908,932 B2
(45) Date of Patent: Mar. 6, 2018

(54) METHODS OF SHIFTING AN ISOELECTRIC PROFILE OF A PROTEIN PRODUCT AND USES THEREOF

(71) Applicant: Alexion Pharmaceuticals, Inc., Cheshire, CT (US)

(72) Inventors: Hunter F. Malanson, Wallingford, CT (US); Pratik Jaluria, Madison, CT (US); Rachael Alford, Cheshire, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 130 days.

(21) Appl. No.: 14/881,799

(22) Filed: Oct. 13, 2015

(65) Prior Publication Data

US 2016/0108111 A1    Apr. 21, 2016

Related U.S. Application Data

(60) Provisional application No. 62/064,397, filed on Oct. 15, 2014.

(51) Int. Cl.
   *C07K 16/18*    (2006.01)
   *G01N 33/68*    (2006.01)
   *C12P 21/02*    (2006.01)

(52) U.S. Cl.
   CPC ............ *C07K 16/18* (2013.01); *C12P 21/02* (2013.01); *G01N 33/6854* (2013.01); *C07K 2317/24* (2013.01); *C07K 2317/76* (2013.01)

(58) Field of Classification Search
   None
   See application file for complete search history.

(56) References Cited

U.S. PATENT DOCUMENTS

| | | |
|---|---|---|
| 6,355,245 B1 | 3/2002 | Evans et al. |
| 2011/0076275 A1 | 3/2011 | Igawa et al. |
| 2012/0164066 A1 | 6/2012 | Greene et al. |
| 2015/0284465 A1 | 10/2015 | Igawa et al. |

OTHER PUBLICATIONS

Bardavid, R. E. et al., "Acid-shifted isoelectric point profiles of the proteins in a hypersaline microbial mat: an adaptation to life at high salt concentrations?" Extremophiles, vol. 16, pp. 787-792 (2012).
Khawli, L. A. et al., "Charge variants in IgG1: Isolation, characterization, in vitro binding properties and pharmacokinetics in rats," mAbs, vol. 2, No. 6, pp. 613-624 (2010).
Kumar, N. et al., "Differential protein expression following low temperature culture of suspension CHO-KI cells," BMC Biotechnology, vol. 8, No. 42, pp. 1-13 (2008).
Liu, H. et al., "Heterogeneity of Monoclonal Antibodies," Journal of Pharmaceutical Sciences, vol. 97, No. 7, pp. 2426-2447 (2008).
International Search Report and Written Opinion for Application No. PCT/US2015/055276, dated Feb. 22, 2016.
An, Z. et al., "IgG2m4, an engineered antibody isotype with reduced Fc function," mAbs, vol. 1(6), pp. 572-579 (2009).
Friedman, D. et al., "Isoelectric Focusing and Two-Dimensional Gel Electrophoresis," Methods Enzymology, vol. 46, pp. 515-540 (2009).
Gebauer, M. et al., "Engineered protein scaffolds as next-generation antibody therapeutics," Current Opinion in Chemical Biology, vol. 13, pp. 245-255 (2009).
Koshel, B. et al., "Trajectory of isoelectric focusing from gels to capillaries to immobilized gradients in capillaries," Proteomics, vol. 12, pp. 2918-2926 (2012).
Righetti, P. et al., "Conventional Isoelectric Focusing in Gel Slabs and Capillaries and Immobilized pH Gradients," Methods Biochem Anal, vol. 54, pp. 379-409 (2011).
Shimura, K., "Recent advances in IEF in capillary tubes and microchips," Electrophoresis, vol. 30, pp. 11-28 (2009).
Sommer, G. et al., "IEF in microfluidic devices," Electrophoresis, vol. 30, pp. 742-757 (2009).
International Preliminary Report on Patentability, PCT/US2015/055276, dated Apr. 18, 2017, 8 pages.

*Primary Examiner* — Anand Desai
(74) *Attorney, Agent, or Firm* — J. Darrell Fontenot, Esq.; Jane E. Remillard, Esq.; Jill Gorny Sloper, Esq.

(57) ABSTRACT

Provided herein are methods shifting the isoelectric profile of a recombinant protein product and the use of such methods in the manufacture of recombinant protein products. Also provided are recombinant protein products produced by such methods.

16 Claims, 12 Drawing Sheets

SEQUENCE LISTING

```
<160> NUMBER OF SEQ ID NOS: 2

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu

-continued

```
                    85                      90                      95
Thr Phe Gly Gln Gly Thr Lys Val Glu Ile Lys Arg Thr Val Ala Ala
            100                     105                     110

Pro Ser Val Phe Ile Phe Pro Pro Ser Asp Glu Gln Leu Lys Ser Gly
        115                     120                     125

Thr Ala Ser Val Val Cys Leu Leu Asn Asn Phe Tyr Pro Arg Glu Ala
        130                     135                     140

Lys Val Gln Trp Lys Val Asp Asn Ala Leu Gln Ser Gly Asn Ser Gln
145                     150                     155                 160

Glu Ser Val Thr Glu Gln Asp Ser Lys Asp Ser Thr Tyr Ser Leu Ser
            165                     170                     175

Ser Thr Leu Thr Leu Ser Lys Ala Asp Tyr Glu Lys His Lys Val Tyr
            180                     185                     190

Ala Cys Glu Val Thr His Gln Gly Leu Ser Ser Pro Val Thr Lys Ser
        195                     200                     205

Phe Asn Arg Gly Glu Cys
        210
```

METHODS OF SHIFTING AN ISOELECTRIC PROFILE OF A PROTEIN PRODUCT AND USES THEREOF

RELATED APPLICATIONS

This application claims priority to and the benefit of U.S. provisional patent application No. 62/064,397, filed on Oct. 15, 2014, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 25, 2015, is named AXJ-196_SL.txt and is 6,312 bytes in size.

TECHNICAL FIELD

This invention relates to methods cell culture and the manufacture of recombinant proteins.

BACKGROUND

Mammalian cells containing a nucleic acid that encodes a recombinant protein are often used to produce therapeutically or commercially important proteins. The resulting recombinant protein product contains a variety of protein molecules, each having its own set of biophysical properties. For example, a recombinant protein product produced by a mammalian cell culture can have one or more protein subpopulations, with each subpopulation having its own isoelectric point. The isoelectric point of a protein subpopulation can effect one or more of the proteins' net charge, solubility, folding, substrate binding affinity, biological activity, and clearance rate in a human body. In view of the effect of the isoelectric point on proteins, it can be desirable to shift or redistribute the subpopulations within the isoelectric profile of a recombinant protein product. For example, it may be desirable to increase or decrease a level (or quantity) of one or more of the protein subpopulation(s) having a specific isoelectric point in a recombinant protein product relative to a reference or starting isoelectric profile.

SUMMARY

The present invention is based, at least in part, on the discovery that incubating a recombinant protein product for an additional period of time under certain conditions results in a shift in the isoelectric profile of the recombinant protein product. The additional period of time may be measured as occurring after a mammalian cell culture reaches a critical time point, such as an additional period of time during the decline phase of a mammalian cell culture. Thus, the present specification includes methods of shifting an isoelectric profile of a recombinant protein product. Also provided are methods of manufacturing a recombinant protein product and methods of manufacturing a drug substance that include the use of these methods of shifting an isoelectric profile of a recombinant protein product.

Provided herein are methods of shifting the isoelectric profile of a recombinant protein product that include: (a) culturing mammalian cells containing a nucleic acid encoding a recombinant protein in a production bioreactor under conditions sufficient to produce the product for a first period of time that consists of a growth phase and/or a stationary phase of the mammalian cells; (b) assaying the product isoelectric profile at the end of the first period of time; and (c) incubating the product under conditions sufficient to shift the isoelectric profile of the product toward a more acidic profile for a second period of time that consists of at least 6 hours of a decline phase of the mammalian cells, or incubating the product under conditions sufficient to shift the isoelectric profile of the product toward a more basic profile for a second period of time of a decline phase of the mammalian cells; and optionally, (d) assaying the product to determine the isoelectric profile and repeating step (c) if the isoelectric profile requires further shifting. In some embodiments of any of the methods described herein, the product incubated in step (c) includes a mixture of the recombinant protein and the mammalian cells in the culture.

Also provided are methods of shifting the isoelectric profile of a recombinant protein product that include: (a) culturing mammalian cells containing a nucleic acid encoding a recombinant protein in a production bioreactor under conditions sufficient to produce the product for a first period of time that includes a growth phase of the mammalian cells and terminates at a critical time point; (b) incubating the product under conditions sufficient to shift the isoelectric profile of the product toward a more acidic profile for a second period of time that consists of at least 6 hours of a decline phase of the mammalian cells; and optionally (c) assaying the product to determine the isoelectric profile and repeating step (b) if the isoelectric profile requires further shifting toward a more acidic profile.

Also provided are methods of shifting the isoelectric profile of a recombinant protein product that include: (a) culturing mammalian cells containing a nucleic acid encoding a recombinant protein in a production bioreactor under conditions sufficient to produce the product for a first period of time that that includes a growth phase of the mammalian cells and terminates at a critical time point; (b) incubating the product under conditions sufficient to shift the isoelectric profile of the product toward a more basic profile for a second period of time of a decline phase of the mammalian cells; and optionally (c) assaying the product to determine the isoelectric profile and repeating step (b) if the isoelectric profile requires further shifting toward a more basic profile.

In some embodiments of any of the methods described herein, step (a) can include fed batch culturing the mammalian cells. In some embodiments of any of the methods described herein, the first period of time is between about 5 days and about 12 days. In some embodiments of any of the methods described herein, the second period of time is between about 6 hours and about 120 hours.

In some embodiments of any of the methods described herein, the product incubated in step (b) includes a mixture of the recombinant protein and the mammalian cells in the culture. In some embodiments of any of the methods described herein, the product is incubated in the production bioreactor. In some embodiments in any of the methods described herein, the product is incubated in a storage vessel.

Some embodiments of any of the methods described herein further include between steps (b) and (c) a step of clarifying the culture and where the product incubated in step (c) includes the recombinant protein in a clarified tissue culture medium. In some embodiments of any of the methods described herein, the method further includes between steps (a) and (b) a step of clarifying the culture and where the product incubated in step (b) includes the recombinant protein in a clarified tissue culture medium. In some embodiments of any of the methods described herein, the product is incubated in a storage vessel.

Some embodiments of any of the methods described herein further include between steps (b) and (c) a step of purifying the recombinant protein and where the product incubated in step (c) includes the purified recombinant protein in a diluent. Some embodiments of any of the methods described herein further include between steps (a) and (b) a step of purifying the recombinant protein and where the product incubated in step (b) includes the purified recombinant protein in a diluent.

In some embodiments of any of the methods described herein, step (a) can include fed batch culturing the mammalian cells under at least one condition that produces a product having a basic profile, and step (c) shifts the product to a more acidic profile. In some embodiments of any of the methods described herein, step (a) can include fed batch culturing the mammalian cells under at least one condition that produces a product having a basic profile, and step (b) shifts the product to a more acidic profile. In some embodiments of any of the methods described herein, the condition includes culturing in a culture media that includes New Zealand bovine serum.

In some embodiments of any of the methods described herein, step (a) can include fed batch culturing the mammalian cells under at least one condition that produces a product having an acidic profile, and step (c) shifts the product to a more basic profile. In some embodiments of any of the methods described herein, step (a) can include fed batch culturing the mammalian cells under at least one condition that produces a product having an acidic profile and step (b) shifts the product to a more basic profile. In some embodiments of any of the methods described herein, the conditions sufficient to shift the isoelectric profile of the product toward a more acidic profile include incubating in a dissolved oxygen ($dO_2$) concentration of between about 20% to about 45% (e.g., between about 25% and about 40% or between about 30% and about 35%).

In some embodiments of any of the methods described herein, the conditions sufficient to shift the isoelectric profile of the product toward a more acidic profile include incubating in a medium having a pH of between about 7.0 and about 7.3 (e.g., between about 7.0 and about 7.25, between about 7.0 and about 7.20, or between about 7.0 and about 7.15).

In some embodiments of any of the methods described herein, the conditions sufficient to shift the isoelectric profile of the product toward a more acidic profile include incubating at a temperature of between about 30° C. and about 37.5° C. (e.g., between about 33° C. and about 37.5° C.). In some embodiments of any of the methods described herein, the conditions sufficient to shift the isoelectric profile of the product to a more acidic profile include incubating at an agitation rate of between about 200 RPM and about 400 RPM (e.g., between about 220 RPM and about 350 RPM or between about 220 RPM and about 300 RPM).

In some embodiments of any of the methods described herein, step (b) and/or (d) can include isoelectric focusing electrophoresis. In some embodiments of any of the methods described herein, step (c) can include isoelectric focusing electrophoresis. In some embodiments of any of the methods described herein, the isoelectric focusing electrophoresis is capillary electrophoresis or gel electrophoresis.

In some embodiments of any of the methods described herein, the recombinant protein is an immunoglobulin, an enzyme, a protein, or an engineered protein. In some embodiments of any of the methods described herein, the recombinant protein is an antibody (such as a human or humanized antibody). In some embodiments of any of the methods described herein, the antibody binds specifically to human complement protein C5 (such as eculizumab). In some embodiments of any of the methods described herein, eculizumab includes a heavy chain including SEQ ID NO: 1 and light chain including SEQ ID NO: 2. In some embodiments of any of the methods described herein, eculizumab includes a heavy chain consisting of SEQ ID NO: 1 and a light chain consisting of SEQ ID NO: 2.

Some embodiments of any of the methods described herein further include (e) formulating the product into a pharmaceutical composition. Some embodiments of any of the methods described herein further include (d) formulating the product into a pharmaceutical composition.

In some embodiments of any of the methods described herein, the isoelectric profile of the recombinant protein product includes seven protein subpopulations having an isoelectric point of between about 5.2 and about 6.7. In some embodiments of any of the methods described herein, incubating the product under conditions sufficient to shift the isoelectric profile of the product toward a more acidic profile results in an increase in the quantity of at least two of the more acidic protein subpopulations and a decrease in the quantity of at least two of the more basic protein subpopulations of the seven protein subpopulations. In some embodiments of any of the methods described herein, the at least two of the more acidic protein subpopulations can be the fourth and fifth most acidic protein subpopulations of the seven protein subpopulations having an isoelectric point of between about 5.2 and about 6.7. In some embodiments of any of the methods described herein, the at least two of the more basic subpopulations can be the first and second most basic protein subpopulations of the seven protein subpopulations having an isoelectric point of between about 5.2 and about 6.7. In some embodiments of any of the methods described herein, the seven protein subpopulations have an isoelectric point of between about 5.45 and about 6.55.

Also provided herein are methods of shifting the isoelectric profile of a recombinant protein product having seven protein subpopulations with an isoelectric point between about 5.45 and about 6.55 that include: (a) fed batch culturing mammalian cells including a nucleic acid encoding a recombinant protein in a production bioreactor under conditions sufficient to produce the product for a first period of time that consists of a growth phase or a growth phase and a stationary phase of the mammalian cells; (b) incubating the product under conditions sufficient to shift the isoelectric profile of the product toward a more acidic profile for a second period of time that consists of at least 6 hours of a decline phase of the mammalian cells, where the more acidic profile includes an increase in the quantity of the fourth and fifth most acidic protein subpopulations of the seven protein subpopulations, and a decrease in the quantity of the first and second most basic protein subpopulations of the seven protein subpopulations; and optionally (c) assaying the product to determine the isoelectric profile and repeating step (b) if the isoelectric profile requires further shifting toward the more acidic profile.

Also provided are methods of shifting the isoelectric profile of a recombinant protein product having seven protein subpopulations with an isoelectric point between about 5.45 and about 6.5 that include: (a) fed batch culturing mammalian cells containing a nucleic acid encoding a recombinant protein in a production bioreactor under conditions sufficient to produce the product for a first period of time that includes a growth phase of the mammalian cells and terminates at a critical time point; (b) incubating the product under conditions sufficient to shift the isoelectric profile of the product toward a more acidic profile for a second period of time that consists of at least 6 hours of a decline phase of the mammalian cells, where the more acidic profile includes an increase in the quantity of the fourth and fifth most acidic protein subpopulations of the seven protein subpopulations, and a decrease in the quantity of the first and second most basic protein subpopulations of the seven protein subpopulations; and optionally (c) assaying the product to determine the isoelectric profile and repeating step (b) if the isoelectric profile requires further shifting toward the more acidic profile.

In some embodiments of any of the methods described herein, the more acidic profile is an isoelectric profile, where: the quantity of protein populating each of the second, third, and fourth most basic protein subpopulations of the seven protein subpopulations is ≥10% of the total mass of protein in the profile; the quantity of protein populating each of the third and fourth most basic protein subpopulations of the seven protein subpopulations is less than the quantity of the second most basic protein subpopulation of the seven protein subpopulations; the quantity of protein populating the most acidic protein subpopulation of the seven protein subpopulations is ≤3% of the total mass of protein in the profile; the quantity of protein populating the second most acidic protein subpopulation of the seven protein subpopulations is ≤6% of the total mass of protein in the profile; the quantity of protein populating the third most acidic protein subpopulation of the seven protein subpopulations is ≤9% of the total mass of protein in the profile; the quantity of protein populating the most basic protein subpopulation of the seven protein subpopulations is ≤8% of the total mass of protein in the profile; and there are no other protein subpopulations having a quantity of protein of ≤6% of the total mass of protein, other than the most acidic, the second most acidic, the third most acidic, and the most basic protein subpopulations of the seven protein subpopulations. In some embodiments of any of the methods described herein, the incubating in (b) can result in recombinant protein product having the more acidic profile.

Also provided are recombinant protein products produced by a method that includes: (a) culturing mammalian cells containing a nucleic acid encoding a recombinant protein in a production bioreactor under conditions sufficient to produce the product for a first period of time that consists of a growth phase and/or a stationary phase of the mammalian cells; (b) assaying the product at the end of the first period of time to the isoelectric profile; and (c) incubating the product under conditions sufficient to shift the isoelectric profile of the product toward a more acidic profile for a second period of time that consists of at least 6 hours of a decline phase of the mammalian cells, or incubating the product under conditions sufficient to shift the isoelectric profile of the product toward a more basic profile for a second period of time of a decline phase of the mammalian cells; and optionally, (d) assaying the product to determine the isoelectric profile and repeating step (c) if the isoelectric profile requires further shifting.

Also provided are recombinant protein products produced by a method that includes: (a) culturing mammalian cells containing a nucleic acid encoding a recombinant protein in a production bioreactor under conditions sufficient to produce the product for a first period of time that includes a growth phase of the mammalian cells and terminates at a critical time point; (b) incubating the product under conditions sufficient to shift the isoelectric profile of the product toward a more acidic profile for a second period of time that consists of at least 6 hours of a decline phase of the mammalian cells; and optionally (c) assaying the product to determine the isoelectric profile and repeating step (b) if the isoelectric profile requires further shifting toward a more acidic profile.

Also provided are recombinant protein products produced by a method that includes: (a) culturing mammalian cells containing a nucleic acid encoding a recombinant protein in a production bioreactor under conditions sufficient to produce the product for a first period of time that that includes a growth phase of the mammalian cells and terminates at a critical time point; (b) incubating the product under conditions sufficient to shift the isoelectric profile of the product toward a more basic profile for a second period of time of a decline phase of the mammalian cells; and optionally (c) assaying the product to determine the isoelectric profile and repeating step (b) if the isoelectric profile requires further shifting toward a more basic profile.

As used herein, the word "a" or "plurality" before a noun represents one or more of the particular noun. For example, the phrase "a mammalian cell" represents "one or more mammalian cells."

The term "isoelectric profile" is known in the art and refers to the use of isoelectric focusing to separate the components of a protein product in solution into subpopulations with discrete isoelectric points. Proteins in solution are comprised of a population of molecules having some varying amount of chemical modifications. In general, for isoelectric focusing, a pH gradient is established and a sample of protein comprising a population of protein molecules is introduced. The individual protein molecules in the sample population are able to migrate to a point that corresponds to their individual isoelectric point (pI). The isoelectric profile of a protein product can be determined using techniques known in the art, such as isoelectric focusing electrophoresis, capillary electrophoresis, or gel electrophoresis. In some instances, an isoelectric profile refers to the population distribution of substantially all of the members of the protein population of a protein product within a pH gradient. In other instances, an isoelectric profile refers to a subset of the members or a subset of the subpopulations of the protein population of a protein product. An isoelectric profile can include 1, 2, 3, 4, 5, or 6, or more subpopulations (e.g., isoelectric protein bands) of a protein product, where each has a different pI. Each band in an isoelectric profile represents a subpopulation of molecules having a pI corresponding to the pH at the point in the gradient where the band is located.

The term "recombinant protein" is known in the art and refers to a protein manufactured using a cell culture system. The cells may be derived from any of a mammalian cell, an insect cell, a yeast cell, or a bacterial cell, where in general, the cells in the cell culture contain an introduced nucleic acid encoding the recombinant protein of interest. The nucleic acid encoding the recombinant protein may also contain a heterologous promoter operably linked to a nucleic acid encoding the protein.

The term "recombinant protein product" refers to a composition comprising a recombinant protein manufactured using a cell culture system. In some instances, the product can include multiple members of the recombinant protein that possess slightly different biophysical properties arising from chemical modifications and degradation processes, and result in subpopulations with discrete isoelectric points. A recombinant protein product can be, e.g., recombinant protein in a clarified tissue culture medium, a purified recombinant protein in a diluent, or a mixture of the recombinant protein, liquid culture medium, and mammalian cells in a culture.

The term "production bioreactor" as used herein refers to a vessel suitable for incubating a mammalian cell culture under conditions sufficient for growth of the mammalian cells in the culture and production of a recombinant protein product by the mammalian cells in the culture. Non-limiting examples of production bioreactors are described herein. Additional examples of production bioreactors are known in the art.

The phrase "conditions sufficient to produce a product" refers to a set of physical parameters, such as temperature, dissolved oxygen, media composition, mixing rate, and cell density, that allows for the production of a recombinant protein by a mammalian cell culture. Non-limiting examples of conditions sufficient to produce a product are known in the art. Some examples of conditions sufficient to produce a product are described herein.

The term "growth phase" as used herein, refers to a period of time during the culturing of a mammalian cell where the viable cell density increases over time. This is in contrast to the lack of substantial change in viable cell density observed over time during the stationary phase or the decrease in viable cell density observed over time during the decline phase of a cell culture.

The term "stationary phase" is known in the art of cell culturing and refers to a period of time in cell culturing where the viable cell density remains substantially the same.

The phrase "decline phase of the mammalian cells" as used herein refers to a period of time in cell culture where the viable cell density begins to decrease.

The phrase "assaying the product" as used herein refers to performing an analytical method to determine one or more physical and/or functional properties of the product (e.g., a recombinant protein product). Non-limiting examples of physical properties include molecular weight, protein sequence, isoelectric profile, percent aggregation, glycosylation fingerprint, phosphorylation, acylation, fragmentation, and denaturation. Non-limiting examples of functional properties of a product that can be determined include enzyme activity, binding specificity, and binding affinity.

The phrase "conditions sufficient to shift the isoelectric profile" refers to a set of parameters (e.g., one or more of time, temperature, pH, agitation rate, $CO_2$, temperature, $dO_2$, and/or reagents present in the tissue culture medium) that can be used to change (e.g., an acidic shift or a basic shift) the isoelectric profile of the product (e.g., a recombinant protein product).

The phrase "shifting to a more acidic profile" as used herein refers to applying conditions sufficient to shift the isoelectric profile of the product to a more acidic profile as compared to the profile of the product in the absence of applying those conditions.

The phrase "shifting to a more basic profile" as used herein refers to applying conditions sufficient to shift the isoelectric profile of the product to a more basic profile as compared to the profile of the product in the absence of applying those conditions.

The term "critical time point" as used herein refers to a time point at which a cell culture (e.g., a fed batch culture) is recognized as beginning to significantly deteriorate in viability. After this point, quality attributes of the recombinant protein may be increasingly negatively affected. For example, after viable cell density peaks in a fed batch bioreactor, the viable cell density will begin to decline. The critical time point may be linked to a certain viable cell density in the decline phase of cell growth. The critical time point may be based on the time the viable cell density decreases to a certain viable cell density, e.g., $15 \times 10^5$ cells/mL, in the decline phase. Similarly, for a particular process the critical time point may be set at other values, e.g., the time the viable cell density decreases to a viable cell density such as $10 \times 10^5$ cells/mL, $11 \times 10^5$ cells/mL, $12 \times 10^5$ cells/mL, $13 \times 10^5$ cells/mL, $14 \times 10^5$ cells/mL, $16 \times 10^5$ cells/mL, $17 \times 10^5$ cells/mL, $18 \times 10^5$ cells/mL, $19 \times 10^5$ cells/mL, $20 \times 10^5$ cells/mL, $30 \times 10^5$ cells/mL, $40 \times 10^5$ cells/mL, or $50 \times 10^5$ cells/mL, in the decline phase.

The term "storage vessel" as used herein refers to a closed container that can be used to incubate a recombinant protein product (e.g., any of the recombinant protein products described herein) under a set of physical conditions that provide for a shift in the isoelectric profile of the recombinant protein product. Non-limiting examples of physical conditions that provide for a shift in the isoelectric profile of a recombinant protein product are described herein.

The term "clarifying a culture" as used herein refers to removing or separating mammalian cells from a mammalian cell culture to yield a liquid culture medium that is substantially-free of mammalian cells (i.e., a clarified tissue culture medium). Non-limiting examples of methods of clarifying a culture are described herein. Additional methods for clarifying a culture are known in the art.

The term "clarified tissue culture medium" as used herein refers to a liquid culture medium used in a cell culture that has been processed, such that it is substantially-free of mammalian cells.

The term "New Zealand bovine serum albumin" as used herein refers to a serum protein derived from a bovine born and bred in New Zealand (e.g., a bovine born and raised in a population free of bovine spongiform encephalopathy (BSE) or other known prion disease). Skilled practitioners will appreciate that such serum albumin is commercially available.

The term "mammalian cell" refers to any cell from or derived from any mammal including, for example, a human, a hamster, a mouse, a green monkey, a rat, a pig, a cow, a hamster, or a rabbit. In some embodiments, the mammalian cell can be an immortalized cell, a differentiated cell, or an undifferentiated cell.

The term "substantially free" as used herein refers to a composition (e.g., a liquid culture medium) that is at least or about 90% free, or about 95%, 96%, 97%, 98%, or at least or about 99% free, or about 100% free of a specific substance.

The term "culturing" or "cell culturing" as used herein refers to maintenance or growth of a mammalian cell in a liquid culture medium under a controlled set of physical conditions.

The term "liquid culture medium" or "culture medium" refers to a fluid that contains sufficient nutrients to allow a mammalian cell to grow in the medium in vitro. For example, a liquid culture medium can include one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, selenium, and other necessary trace metals, and sodium bicarbonate. A liquid culture medium may include serum or serum components from a mammal. In some instances, a liquid culture medium does not contain serum or another extract from a mammal (a chemically-defined liquid culture medium). A liquid culture medium may contain trace metals, a mammalian growth hormone, and/or a mammalian growth factor. Non-limiting examples of liquid culture medium are described herein and additional examples are known in the art and are commercially available.

The term "animal-derived component free liquid culture medium" refers to a liquid culture medium that does not contain any components (e.g., proteins or serum) derived from an animal.

The term "serum-free liquid culture medium" refers to a liquid culture medium that does not contain animal serum.

The term "serum-added liquid culture medium" refers to a liquid culture medium that includes animal serum.

The term "chemically-defined liquid culture medium" refers to a liquid culture medium in which substantially all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" refers to a liquid culture medium that does not contain any protein (e.g., any detectable protein).

"Rotary agitation" is a term well-known in the art and refers to the agitation of a culture in a bioreactor (e.g., a production bioreactor) in a generally circular fashion, e.g., clock-wise or counter-clockwise, in order to, e.g., increase the dissolved $O_2$ concentration in the culture in the bioreactor. Agitation can be performed using any method known in the art, e.g., an instrument that moves the culture in a circular or ellipsoidal motion, such as an impellor. Exemplary devices that can be used to perform rotary agitation are known in the art and are commercially available.

The term "immunoglobulin" refers to a polypeptide containing an amino acid sequence of at least 15 amino acids (e.g., at least 20, 30, 40, 50, 60, 70, 80, 90, or 100 amino acids, or more than 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin, such as a CDRH3. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')$_2$ fragment, or an scFv. The immunoglobulin may also be a bi-specific antibody or a tri-specific antibody, or a dimer, trimer, or multimer antibody, or a diabody, a DVD-Ig, a CODV-Ig, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" refers to a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length.

The term "engineered protein" refers to a polypeptide that is not naturally encoded by an endogenous nucleic acid present within an organism (e.g., a mammal). Examples of engineered proteins include modified enzymes with one or more amino acid substitutions, deletions, insertions, or additions that result in an increase in stability and/or catalytic activity of the engineered enzyme, fusion proteins, humanized antibodies, chimeric antibodies, divalent antibodies, trivalent antibodies, four binding domain antibodies, a diabody, and antigen-binding proteins that contain at least one recombinant scaffolding sequence.

The term "purify" or "purifying" in certain contexts means at least partially isolating a recombinant protein from one or more other components (e.g., DNA, RNA, or other proteins) present in the cell culture medium or cell culture lysate. The extent of purification can be specified, such as at least or about 5%, e.g., at least or about 10%, 15%, 20%, 25%, 30%, 40%, 45%, 50%, 55%, 60%, 65%, 70%, 75%, 80%, 85%, 90%, or at least or about 95% to 99.9% pure by weight. Non-limiting methods for recovering a protein from a liquid culture medium or from a mammalian cell lysate are described herein and others are known in the art.

The term "secreted protein" or "secreted recombinant protein" refers to a recombinant protein that originally included a secretion signal sequence when it is translated within a mammalian cell. The signal sequence is usually removed through enzymatic cleavage in the mammalian cell and the protein is released into the extracellular space (e.g., a liquid culture medium).

The phrase "gradient perfusion" as used herein refers to the incremental change (e.g., increase or decrease) in the volume of culture medium removed and added to an initial cell culture over incremental time periods. The periods may be about a 24-hour period, or a period of between about 1 minute and about 24-hours, or a period of greater than 24 hours) during the first period of time in a culture method that utilizes perfusion culturing (e.g., the culture medium re-feed rate on a daily basis). The fraction of media removed and replaced each day can vary depending on the particular cells being cultured, the initial seeding density, and the cell density at a particular time.

The term "fed batch cell culture" or "fed batch culturing" means the incremental or continuous addition of a second culture medium (e.g., liquid or solid culture medium) to an initial cell culture without substantial or significant removal of the first liquid culture medium from the cell culture. In some instances, the second liquid culture medium is the same as the first liquid culture medium. In other instances, the second liquid culture medium is a concentrated form of the first liquid culture medium and/or is added as a dry powder.

"Specific productivity rate" or "SPR" as used herein refers to the mass or enzymatic activity of a recombinant protein produced per mammalian cell per day. The SPR for a recombinant antibody is usually measured as mass/cell/day. The SPR for a recombinant enzyme is usually measured as units/cell/day or (units/mass)/cell/day.

"Volume productivity rate" or "VPR" as used herein refers to the mass or enzymatic activity of recombinant protein produced per volume of culture (e.g., per L of bioreactor, vessel, or tube volume) per day. The VPR for a recombinant antibody is usually measured as mass/L/day. The VPR for a recombinant enzyme is usually measured as units/L/day or mass/L/day.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
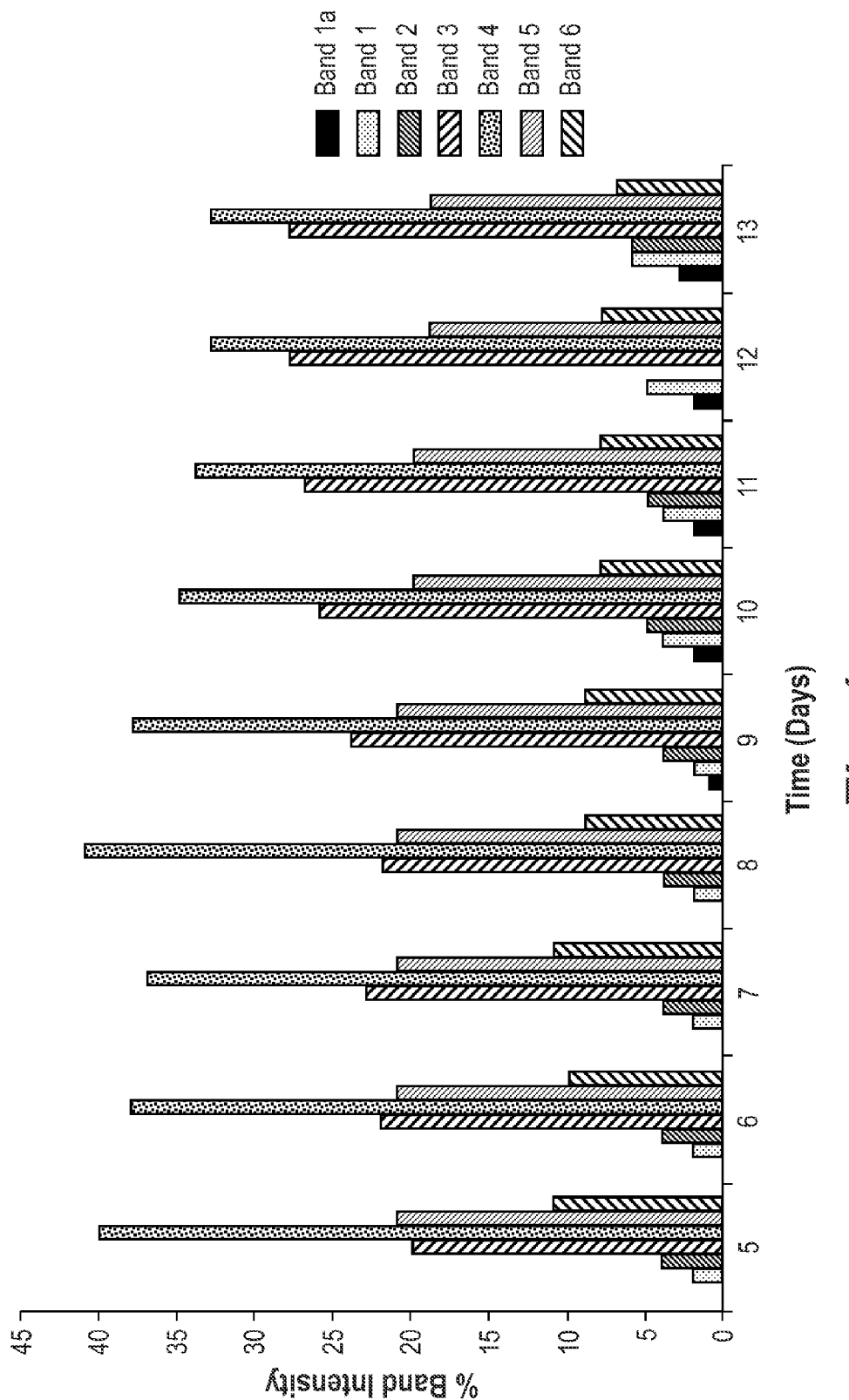
FIG. 1 is a graph of the percentage of band intensity for each band in the isoelectric profile of eculizumab produced by a first fed batch culture run performed using a 10,000-L bioreactor from day 5 to day 13.

Provided herein are methods of shifting the isoelectric profile of a recombinant protein product. The methods described herein can achieve a recombinant protein product that has a desired isoelectric profile. For example, a recombinant protein having a desired isoelectric profile can have one or more of: an optimal net charge (e.g., net surface charge), decreased level of precipitation (as compared to the same recombinant protein having a different isoelectric profile at the same pH), increased solubility in a desired fluid (as compared to the same recombinant protein having a different isoelectric profile in the same fluid and under the same conditions), an increased biological activity (e.g., binding to a substrate, target, or antigen, binding specificity, or enzymatic activity as compared to the same recombinant protein having a different isoelectric profile and tested under the same conditions), an increased level of properly folded protein in the recombinant protein product (as compared to the level of properly folded protein in the same recombinant protein having a different isoelectric profile when tested under the same conditions), and a decreased clearance rate in the body of a human (as compared to the clearance rate of the same recombinant protein having a different isoelectric profile, when tested under the same conditions). Non-limiting aspects of the methods of shifting the isoelectric profile of a recombinant protein product are described below. Any of the aspects described below can be used in any combination or with any other elements known in the art.

Isoelectric Profiles and Methods of Determining Isoelectric Profile

An isoelectric profile refers to the acidic and/or basic nature of at least one subpopulation of the protein population of a protein product. An isoelectric profile can also refer to the quantity of protein in one or more subpopulations in a protein product. In some examples, the isoelectric profile refers to the acidic and/or basic nature of at least two protein subpopulations of a protein product (e.g., a recombinant protein product), where each of the at least two protein subpopulations has a different isoelectric point as compared to other protein subpopulations in the protein product. An isoelectric profile can refer to the acidic and/or basic nature of all of the protein subpopulations detected in a recombinant protein product, or an isoelectric profile can refer to the acidic and/or basic nature of a subset of at least 2 of the protein subpopulations detected for a recombinant protein product. For example, an isoelectric profile can refer to the acidic and/or basic nature of at least 1, 2, 3, 4, 5, 6, 7, 8, 9, 10, 11, 12, 13, 14, or 15 protein subpopulations. Such protein subpopulations are referred to as bands in an isoelectric focusing gel.

An isoelectric profile of a recombinant protein product can include protein subpopulations having an isoelectric point of between about pH 4.0 and pH 7.3 (e.g., between about pH 4.1 and about pH 7.3, between about pH 4.2 and about pH 7.3, between about pH 4.3 and about pH 7.3, between about pH 4.4 and about pH 7.3, between about pH 4.5 and about pH 7.3, between about pH 4.6 and about pH 7.3, between about pH 4.7 and about pH 7.3, between about pH 4.8 and about pH 7.3, between about pH 4.9 and about pH 7.3, between about pH 5.0 and about pH 7.3, between about pH 5.1 and about pH 7.3, between about pH 5.2 and about pH 7.3, between about pH 5.3 and about pH 7.3, between about pH 5.4 and about pH 7.3, between about pH 5.5 and about pH 7.3, between about pH 5.6 and about pH 7.3, between about pH 5.7 and about pH 7.3, between about pH 5.8 and about pH 7.3, between about pH 5.9 and about pH 7.3, between about pH 6.0 and about pH 7.3, between about pH 6.1 and about pH 7.3, between about pH 6.2 and about pH 7.3, between about pH 6.3 and about pH 7.3, between about pH 6.4 and about pH 7.3, between about pH 6.5 and about pH 7.3, between about pH 6.6 and about pH 7.3, between about pH 6.7 and about pH 7.3, between about pH 4.0 and about pH 7.0, between about pH 4.1 and about pH 7.0, between about pH 4.2 and about pH 7.0, between about pH 4.3 and about pH 7.0, between about pH 4.4 and about pH 7.0, between about pH 4.5 and about pH 7.0, between about pH 4.6 and about pH 7.0, between about pH 4.7 and about pH 7.0, between about pH 4.8 and about pH 7.0, between about pH 4.9 and about pH 7.0, between about pH 5.0 and about pH 7.0, between about pH 5.1 and about pH 7.0, between about 5.2 and about pH 7.0, between about pH 5.3 and about pH 7.0, between about pH 5.4 and about pH 7.0, between about pH 5.5 and about pH 7.0, between about pH 5.6 and about pH 7.0, between about pH 5.7 and about pH 7.0, between about pH 5.8 and about pH 7.0, between about pH 5.9 and about pH 7.0, between about pH 6.0 and about pH 7.0, between about pH 6.1 and about pH 7.0, between about pH 6.2 and about pH 7.0, between about pH 6.3 and about pH 7.0, between about pH 6.4 and about pH 7.0, between about pH 6.5 and about pH 7.0, between about pH 4.0 and about pH 6.8, between about pH 4.1 and about pH 6.8, between about pH 4.2 and about pH 6.8, between about pH 4.3 and about pH 6.8, between about pH 4.4 and about pH 6.8, between about pH 4.5 and about pH 6.8, between about pH 4.6 and about pH 6.8, between about pH 4.7 and about pH 6.8, between about pH 4.8 and about pH 6.8, between about pH 4.9 and about pH 6.8, between about pH 5.0 and about pH 6.8, between about pH 5.1 and about pH 6.8, between about pH 5.2 and about pH 6.8, between about pH 5.3 and about pH 6.8, between about pH 5.4 and about pH 6.8, between about pH 5.5 and about pH 6.8, between about pH 5.6 and about pH 6.8, between about pH 5.7 and about pH 6.8, between about pH 5.8 and about pH 6.8, between about pH 5.9 and about pH 6.8, between about pH 6.0 and about pH 6.8, between about pH 6.1 and about pH 6.8, between about pH 6.2 and about pH 6.8, between about pH 6.3 and pH 6.8, between about pH 4.0 and about pH 6.6, between about pH 4.1 and about pH 6.6, between about pH 4.2 and about pH 6.6, between about pH 4.3 and about pH 6.6, between about pH 4.4 and about pH 6.6, between about pH 4.5 and about pH 6.6, between about pH 4.6 and about pH 6.6, between about pH 4.7 and about pH 6.6, between about pH 4.8 and about pH 6.6, between about pH 4.9 and about pH 6.6, between about pH 5.0 and about pH 6.6, between about pH 5.1 and about pH 6.6, between about pH 5.2 and about pH 6.6, between about pH 5.3 and about pH 6.6, between about pH 5.4 and about pH 6.6, between about pH 5.5 and about pH 6.6, between about pH 5.6 and about pH 6.6, between about pH 5.7 and about pH 6.6, between about pH 5.8 and about pH 6.6, between about pH 5.9 and about pH 6.6, between about pH 6.0 and about pH 6.6, or between about pH 6.1 and about pH 6.6.

An isoelectric profile of a recombinant protein product can include protein subpopulations having an isoelectric points of between about pH 6.0 and pH 9.0, between about pH 6.2 and about pH 9.0, between about pH 6.4 and about pH 9.0, between about pH 6.6 and about pH 9.0, between about pH 6.8 and about pH 9.0, between about pH 7.0 and about pH 9.0, between about pH 7.2 and about pH 9.0, between about pH 7.4 and pH 9.0, between about pH 7.6 and about pH 9.0, between about pH 7.8 and about pH 9.0, between about pH 8.0 and about pH 9.0, between about pH 8.2 and about pH 9.0, between about pH 8.4 and about pH 9.0, between about pH 6.0 and about pH 8.5, between about pH 6.2 and about pH 8.5, between about pH 6.4 and about pH 8.5, between about pH 6.6 and about pH 8.5, between about pH 6.8 and about pH 8.5, between about pH 7.0 and about pH 8.5, between about pH 7.2 and about pH 8.5, between about pH 7.4 and about pH 8.5, between about pH 7.6 and about pH 8.5, between about pH 7.8 and about pH 8.5, between about pH 8.0 and pH 8.5, between about pH 6.0 and about 8.0, between about pH 6.2 and about pH 8.0, between about pH 6.4 and about pH 8.0, between about pH 6.6 and about pH 8.0, between about pH 6.8 and about pH 8.0, between about pH 7.0 and about pH 8.0, between about pH 7.2 and about pH 8.0, between about pH 7.4 and about pH 8.0, between about pH 6.0 and about pH 7.5, between about pH 6.2 and about pH 7.5, between about pH 6.4 and about pH 7.5, between about pH 6.6 and about pH 7.5, between about pH 6.8 and about pH 7.5, or between about pH 7.0 and about pH 7.5.

Non-limiting examples of an isoelectric profile of eculizumab contain seven or eight protein subpopulations having isoelectric points of between about 5.2 and about 6.7. More particularly, the isoelectric profile of eculizumab contains seven or eight bands having a pI of between about 5.45 and about 6.55, as determined by isoelectric focusing electrophoresis. An additional example of a reference isoelectric profile for eculizumab is described in the Examples.

Methods for determining an isoelectric profile of a recombinant protein product are known in the art. For example, isoelectric focusing gel electrophoresis (e.g., capillary isoelectric focusing gel electrophoresis) and chips are known in the art (see, e.g., the methods described in Righetti et al., *Methods Biochem. Anal.* 54:379-409, 2011; Friedman et al., *Methods Enzymol.* 463:515-540, 2009; Koshel et al., *Proteomics* 12:2918-2926, 2012; Sommer et al., *Electrophoresis* 30:742-757, 2009; Shimura et al., *Electrophoresis* 30:11-28, 2009). Additional methods for determining the isoelectric profile of a recombinant protein are known in the art. Assays to determine the isoelectric profile of a recombinant protein product can include the performance of isoelectric focusing gel electrophoresis (e.g., capillary isoelectric focusing gel electrophoresis). Any of the methods described herein can include one or more steps of determining the isoelectric profile of a recombinant protein product at one or more time points (e.g., at the end of the first period of time, at the end of the second period of time, or at one or more time points during the second period of time). In some embodiments, the recombinant protein product is purified prior to analysis of the isoelectric profile. The recombinant protein may be purified from a tissue culture medium or a clarified tissue culture medium. In some examples, the recombinant protein product is stored at a temperature of about 15° C., about 10° C., about 4° C., 0° C., −20° C., −70° C., or −80° C. for a period of time. The storage time is usually less than 24 hours, less than 48 hours, less than 3 days, less than 4 days, or less than one week, prior to performing an assay to determine the isoelectric profile of the recombinant protein product.

A reference isoelectric profile in any of the methods described herein can be an isoelectric profile before incubating under conditions sufficient to shift the isoelectric profile of the product toward a more acidic profile or a more basic profile or an isoelectric profile of a recombinant protein product having one or more beneficial biophysical properties. Beneficial biophysical properties can include increased solubility, increased enzymatic or binding activity, increased half-life in vivo, and decreased clearance in vivo. A non-limiting example of a reference isoelectric profile for eculizumab is described herein.

Culturing Mammalian Cells

The methods described herein include a step of culturing mammalian cells including a nucleic acid encoding a recombinant protein in a production bioreactor under conditions sufficient to produce the product for a first period of time. For example, the first period of time comprises, consists, or consists essentially of a growth phase and a stationary phase. The first period of time usually includes a growth phase and a stationary phase. In some embodiments, the first period of time includes a portion of the decline phase of growth. In some embodiments, the mammalian cells are cultured under conditions sufficient to produce the product and promote division of the mammalian cells for the first period of time. Non-limiting examples of the aspects of culturing mammalian cells that can be used in the methods described herein are described below.

Fed Batch Culturing

The culturing step in the methods described herein can include fed batch culturing. As is known in the art, fed batch culturing includes the incremental or continuous addition of a second culture medium to an initial cell culture without substantial or significant removal of the first liquid culture medium from the cell culture. In some instances, the second culture medium is the same as the first liquid culture medium. The second culture medium may be either in a liquid form or a dry powder. In other instances, the second culture medium is a concentrated form of the first liquid culture medium and/or is added as a dry powder.

The second culture medium can be added to the initial cell culture at a specific time point or at multiple time points during the first period of time. For example, the second culture medium can be added to the initial cell culture at a time point that is between 6 hours and 7 days, between about 6 hours and about 6 days, between about 6 hours and about 5 days, between about 6 hours and about 4 days, between about 6 hours and about 3 days, between about 6 hours and about 2 days, between about 6 hours and about 1 day, between about 12 hours and about 7 days, between about 12 hours and about 6 days, between about 12 hours and about 5 days, between about 12 hours and about 4 days, between about 12 hours and about 3 days, between about 12 hours and about 2 days, between about 1 day and about 7 days, between about 1 day and about 6 days, between about 1 day and about 5 days, between about 1 day and about 4 days, between about 1 day and about 3 days, between about 1 day and about 2 days, between about 2 days and about 7 days, between about 2 days and about 6 days, between about 2 days and about 5 days, between about 2 days and about 4 days, between about 2 days and about 3 days, between about 3 days and about 7 days, between about 3 days and about 6 days, between about 3 days and about 5 days, between about 3 days and about 4 days, between about 4 days and about 7 days, between about 4 days and about 6 days, between about 4 days and about 5 days, between about 5 days and about 7 days, or between about 5 days and about 6 days, after the start of the first period of time.

The second culture medium can be continuously added to the initial cell culture, or can be added periodically (e.g., daily) to the initial cell culture during the first period of time. In some examples when the second culture medium is added periodically to the initial cell culture, the second culture medium can be added once, twice, three times, four times, five times, or six times. The volume of a second liquid culture medium or the amount of a second solid culture medium added to the initial cell culture can change (e.g., increase) during the first period of time. The volume of a second liquid culture medium added to the initial cell culture over any 24 hour period in the first time period can be some fraction of the initial volume of the bioreactor. The volume of a second liquid culture medium added to the initial cell culture over any 24 hour period in the first time period can be between 0.01× and about 0.3× volume of the bioreactor. The faction may be between about 0.01× and about 0.28×, between about 0.01× and about 0.26×, between about 0.01× and about 0.24×, between about 0.01× and about 0.22×, between about 0.01× and about 0.20×, between about 0.01× and about 0.18×, between about 0.01× and about 0.16×, between about 0.01× and about 0.14×, between about 0.01× and about 0.12×, between about 0.01× and about 0.10×, between about 0.01× and about 0.08×, between about 0.01× and about 0.06×, between about 0.01× and about 0.04×, between about 0.025× and about 0.3×, between about 0.025× and about 0.28×, between about 0.025× and about 0.26×, between about 0.025× and about 0.24×, between about 0.025× and about 0.22×, between about 0.025× and about 0.20×, between about 0.025× and about 0.18×, between about 0.025× and about 0.16×, between about 0.025× and about 0.14×, between about 0.025× and about 0.12×, between about 0.025× and about 0.10×, between about 0.025× and about 0.08×, between about 0.025× and about 0.06×, between about 0.025× and about 0.04×, between about 0.05× and about 0.3×, between about 0.05× and about 0.28×, between about 0.05× and about 0.26×, between about 0.05× and about 0.24×, between about 0.05× and about 0.22×, between about 0.05× and about 0.20×, between about 0.05× and about 0.18×, between about 0.05× and about 0.16×, between about 0.05× and about 0.14×, between about 0.05× and about 0.12×, between about 0.05× and about 0.10×, between about 0.1× and about 0.3×, between about 0.1× and about 0.28×, between about 0.1× and about 0.26×, between about 0.1× and about 0.24×, between about 0.1× and about 0.22×, between about 0.1× and about 0.20×, between about 0.1× and about 0.18×, between about 0.1× and about 0.16× between about 0.1× and about 0.14×, between about 0.1×, between about 0.15× and about 0.3×, between about 0.15× and about 0.2×, between about 0.2× and about 0.3×, or between about 0.25× and about 0.3×, of the bioreactor volume.

In other embodiments, the volume of a second liquid culture medium added to the initial cell culture over any 24 hour period in the first period of time can be between 0.02× and about 1.0×, between about 0.02× and about 0.9×, between about 0.02× and about 0.8×, between about 0.02× and about 0.7×, between about 0.02× and about 0.6×, between about 0.02× and about 0.5×, between about 0.02× and about 0.4×, between about 0.02× and about 0.3×, between about 0.02× and about 0.2×, between about 0.02× and about 0.1×, between about 0.05× and about 1.0×, between about 0.05× and about 0.8×, between about 0.05× and about 0.7×, between about 0.05× and about 0.6×, between about 0.05× and about 0.5×, between about 0.05× and about 0.4×, between about 0.05× and about 0.3×, between about 0.05× and about 0.2×, between about 0.05× and about 0.1×, between about 0.1× and about 1.0×, between about 0.1× and about 0.9×, between about 0.1× and about 0.8×, between about 0.1× and about 0.7×, between about 0.1× and about 0.6×, between about 0.1× and about 0.5×, between about 0.1× and about 0.4×, between about 0.1× and about 0.3×, between about 0.1× and about 0.2×, between about 0.2× and about 1.0×, between about 0.2× and about 0.9×, between about 0.2× and about 0.8×, between about 0.2× and about 0.7×, between about 0.2× and about 0.6×, between about 0.2× and about 0.5×, or between about 0.2× and about 0.4× of the volume of the initial cell culture, at the start of the first period of time.

When fed batch culturing is used in the present methods, the first period of time can be between about 4 days and about 12 days, between about 4 days and about 11 days, between about 4 days and about 10 days, between about 4 days and about 9 days, between about 4 days and about 8 days, between about 4 days and about 7 days, between about 4 days and about 6 days, between about 4 days and about 5 days, between about 5 days and about 12 days, between about 5 days and about 11 days, between about 5 days and about 10 days, between about 5 days and about 9 days, between about 5 days and about 8 days, between about 5 days and about 7 days, between about 6 days and about 12 days, between about 6 days and about 11 days, between about 6 days and about 10 days, between about 6 days and about 9 days, between about 6 days and about 8 days, between about 7 days and about 12 days, between about 7 days and about 11 days, between about 7 days and about 10 days, between about 7 days and about 9 days, between about 8 days and about 12 days, between about 8 days and about 11 days, between about 8 days and about 10 days, between about 9 days and about 12 days, between about 9 days and about 11 days, or between about 10 days and about 12 days.

Perfusion Culturing

The culturing step in the methods described herein can be perfusion culturing. As is known in the art, perfusion culturing includes removing from a production bioreactor a first volume of a first liquid culture medium, and adding to the production bioreactor a second volume of a second liquid culture medium, wherein the first volume and the second volume are about equal. The mammalian cells are retained in the bioreactor by some cell retention device or through techniques, such as cell settling in a settling cone. The removal and addition of media in perfusion culturing can be performed simultaneously or sequentially, or some combination of the two. Further, removal and addition can be performed continuously, such as at a rate that removes and replaces a volume of between 0.1% to 800%, between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, or between 4% and 30% of the volume of the production bioreactor.

The first volume of the first liquid culture medium removed and the second volume of the second liquid culture medium added can in some instances be held approximately the same over each 24-hour period. As is known in the art, the rate at which the first volume of the first liquid culture medium is removed (volume/unit of time) and the rate at which the second volume of the second liquid culture medium is added (volume/unit of time) can be varied and depends on the conditions of the particular cell culture system. The rate at which the first volume of the first liquid culture medium is removed (volume/unit of time) and the rate at which the second volume of the second liquid culture medium is added (volume/unit of time) can be about the same or can be different.

Alternatively, the volume removed and added can change by gradually increasing over each 24-hour period. For example, the volume of the first liquid culture medium removed and the volume of the second liquid culture medium added within each 24-hour period can be increased over the culturing period. The volume can be increased over the first period of time from a volume that is between 0.5% to about 20% of the production bioreactor volume. The volume can be increased over the first period of time to about 25% to about 150% of the production bioreactor volume or the first liquid culture medium volume.

In some examples of the methods described herein, after the first 48 to 96 hours of the first period of time, in each 24-hour period (within the first period of time), the first volume of the first liquid culture medium removed and the second volume of the second liquid culture medium added is about 10% to about 95%, about 10% to about 20%, about 20% to about 30%, about 30% to about 40%, about 40% to about 50%, about 50% to about 60%, about 60% to about 70%, about 70% to about 80%, about 80% to about 90%, about 85% to about 95%, about 60% to about 80%, or about 70% of the volume of the first liquid culture medium.

Skilled practitioners will appreciate that the first liquid culture medium and the second liquid culture medium can be the same type of media. In other instances, the first liquid culture medium and the second liquid culture medium can be different. The second liquid culture medium may be more concentrated with respect to one or more media components.

The first volume of the first liquid culture medium can be removed by using any automated system. For example alternating tangential flow filtration may be used. Alternatively, the first volume of the first liquid culture medium can be removed by seeping or gravity flow of the first volume of the first liquid culture medium through a sterile membrane with a molecular weight cut-off that excludes the mammalian cell. Alternatively, the first volume of the first liquid culture medium can be removed by stopping or significantly decreasing the rate of agitation for a period of at least 1 minute, at least 2 minutes, 3 minutes, 4 minutes, 5 minutes, 10 minutes, 15 minutes, 20 minutes, 25 minutes, 30 minutes, 40 minutes, 50 minutes, or 1 hour, and removing or aspirating the first volume of the first liquid culture medium from the top of the production bioreactor.

The second volume of the second liquid culture medium can be added to the first liquid culture medium by a pump. The second liquid culture medium can be added to the first liquid culture medium manually, such as by pipetting or injecting the second volume of the second liquid culture medium directly onto the first liquid culture medium or in an automated fashion.

First Time Period

In the methods described herein, mammalian cells including a nucleic acid encoding a recombinant protein are cultured in a production bioreactor under conditions sufficient to produce the product for a first period of time. In some embodiments, the first period of time consists of a growth phase, or consists or the growth phase and the stationary phase of the mammalian cells. In some embodiments, the first period of time consists of the growth phase, the stationary phase, and a portion of the decline phase of the mammalian cells being cultured. In other examples, the first period of time includes the growth phase of the mammalian cells and terminates at a critical time point. Non-limiting examples of a critical time point are known in the art. For example, a critical time point is a time point whereby the cell culture is beginning to significantly deteriorate in viability and may cause deterioration in the recombinant protein's critical quality attributes. In another example, a critical time point may be a time where the recombinant protein product in the culture medium or cell culture is beginning to significantly deteriorate in a particular quality attribute, such as increased formation of degradation products, increased denaturation, increased formation of undesired glycoforms, increased formation of aggregates, and/or loss in biological activity. Methods for detecting and determining a critical time point for a cell culture depend on the protein being produced and the intended use of the protein product. For example, methods for detecting protein degradation products, denatured recombinant protein, recombinant protein aggregates, and recombinant protein biological activity are well known in the art.

In non-limiting examples, the critical time point is between about 5 days to about 12 days, between about 5 days to about 11 days, between about 5 days to about 10 days, between about 5 days to about 9 days, between about 5 days to about 8 days, between about 5 days to about 7 days, between about 6 days to about 12 days, between about 6 days to about 11 days, between about 6 days to about 10 days, between about 6 days to about 9 days, between about 6 days to about 8 days, between about 7 days to about 12 days, between about 7 days to about 11 days, between about 7 days to about 10 days, between about 7 days to about 9 days, between about 8 days to about 12 days, between about 8 days to about 11 days, between about 8 days to about 10 days, between about 9 days to about 12 days, between about 9 days to about 11 days, or between about 8 days to about 10 days, after the start of the first period of time. Additional examples of critical time points are described in the Examples.

Mammalian Cells

The mammalian cells that are cultured in the methods described herein can be a variety of different mammalian cells. In some examples, the mammalian cell is an adherent cell and the cell culture includes microcarriers. In some examples, the mammalian cell can be a cell that grows in suspension. Non-limiting examples of mammalian cells that can be cultured using the methods described herein include: Chinese hamster ovary (CHO) cells (e.g., CHO DG44 cells, CHO-K1s cells), Sp2/0 myeloma cells, other myeloma cells, such as NS/0 cells, B-cells, hybridoma cells, T-cells, human embryonic kidney (HEK) cells (e.g, HEK 293E and HEK 293F), African green monkey kidney epithelial cells (Vero) cells, and Madin-Darby Canine (Cocker Spaniel) kidney epithelial cells (MDCK) cells. Additional mammalian cells that can be cultured using the methods described herein are known in the art. In non-limiting examples of any of the methods described herein, the cell density of mammalian cells present in the production bioreactor at the start of the first period of time is about $0.1 \times 10^6$ cells/mL to about $0.5 \times 10^6$ cells/mL, about $0.2 \times 10^6$ cells/mL to about $0.4 \times 10^6$ cells/mL, or about $0.25 \times 10^6$ cells/mL to about $0.5 \times 10^6$ cells/mL.

The mammalian cells used in the methods described herein can contain a recombinant nucleic acid that is stably integrated in the mammalian cell's genome and encodes a recombinant protein. In some embodiments, the recombinant protein is secreted by the mammalian cell into the tissue culture medium. In some instances, the cultured mammalian cells are derived from a seed culture. More particularly, the initial cell culture is the result of a seed train process or a culture from another production bioreactor.

Culture Media

Liquid culture media that can be used in the culturing step are known in the art. The liquid culture medium can be supplemented with a mammalian serum or a mammalian serum component, such as a growth hormone or growth factor (e.g., insulin, transferrin, or epidermal growth factor). The mammalian serum or serum component may be fetal bovine serum and it may be derived exclusively from New Zealand bovine serum. Alternatively, the liquid culture medium can be a chemically-defined liquid culture medium, an animal-derived component-free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source from a carbohydrate, such as glucose, amino acids (e.g., the basic set of twenty amino acids plus cysteine), vitamins, free fatty acids, trace elements, and other organic compounds required at low concentrations. The liquid culture medium can be supplemented with salts and buffers (e.g., calcium, magnesium, and phosphate salts), nucleosides and bases (e.g., adenosine, thymidine, and hypoxanthine), protein and tissue hydrolysates, and/or any combination of these or other additives.

Non-limiting examples of liquid culture media that can be useful in the presently described methods include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland). Medium components that also may be useful in the present methods include, but are not limited to, chemically-defined (CD) hydrolysates, e.g., CD peptone, CD polypeptides (two or more amino acids), and CD growth factors. Additional examples of liquid tissue culture medium and medium components are known in the art.

The culture media used in the culturing of the mammalian cells can have a pH of between about 6.5 and about 7.5, between about 6.5 and about 7.4, between about 6.5 and about 7.3, between about 6.5 and about 7.2, between about 6.5 and about 7.1, between about 6.5 and about 7.0, between about 6.5 and about 6.9, between about 6.5 and about 6.8, between about 6.5 and about 6.7, between about 6.6 and about 7.5, between about 6.6 and about 7.4, between about 6.6 and about 7.3, between about 6.6 and about 7.2, between about 6.6 and about 7.1, between about 6.6 and about 7.0, between about 6.6 and about 6.9, between about 6.6 and about 6.8, between about 6.7 and about 7.5, between about 6.7 and about 7.4, between about 6.7 and about 7.3, between about 6.7 and about 7.2, between about 6.7 and about 7.1, between about 6.7 and about 7.0, between about 6.7 and about 6.9, between about 6.8 and about 7.5, between about 6.8 and about 7.4, between about 6.8 and about 7.3, between about 6.8 and about 7.2, between about 6.8 and about 7.1, between about 6.8 and about 7.0, between about 6.9 and about 7.5, between about 6.9 and about 7.4, between about 6.9 and about 7.3, between about 6.9 and about 7.2, between about 6.9 and about 7.1, between about 7.0 and about 7.5, between about 7.0 and about 7.4, between about 7.0 and about 7.3, between about 7.0 and about 7.2, between about 7.1 and about 7.5, between about 7.1 and about 7.4, between about 7.1 and about 7.3, between about 7.2 and about 7.5, between about 7.2 and about 7.4, or between about 7.3 and about 7.5.

Skilled practitioners will appreciate that the liquid culture medium used in culturing can be the same or can change during the first period of time depending on cell culture conditions.

In some embodiments, the culture media added to a fed batch culture can be a solid composition. Examples of solid culture media that can be added to a fed batch culture are known in the art.

Agitation

The culturing of a mammalian cell usually includes some form of agitation for mixing of the culture. For example, the agitation used in culturing can be rotary agitation using an impellar. The agitation can occur at a frequency of at about 200 RPM to about 500 RPM, between about 200 RPM and 480 RPM, between about 200 RPM and about 460 RPM, between about 200 RPM and about 440 RPM, between about 200 RPM and about 420 RPM, between about 200 RPM and about 400 RPM, between about 200 RPM and about 380 RPM, between about 200 RPM and about 360 RPM, between about 200 RPM and about 340 RPM, between about 200 RPM and about 320 RPM, between about 200 RPM and about 300 RPM, between about 200 RPM and about 280 RPM, between about 200 RPM and about 260 RPM, between about 200 RPM and about 240 RPM, between about 200 RPM and about 220 RPM, between about 240 RPM and about 500 RPM, between about 240 RPM and about 480 RPM, between about 240 RPM and about 460 RPM, between about 240 RPM and about 440 RPM, between about 240 RPM and about 420 RPM, between about 240 RPM and about 400 RPM, between about 240 RPM and about 380 RPM, between about 240 RPM and about 360 RPM, between about 240 RPM and about 340 RPM, between about 240 RPM and about 320 RPM, between about 240 RPM and about 300 RPM, between about 240 RPM and about 280 RPM, between about 240 RPM and about 260 RPM, between about 260 RPM and about 500 RPM, between about 260 RPM and about 480 RPM, between about 260 RPM and about 460 RPM, between about 260 RPM and about 440 RPM, between about 260 RPM and about 420 RPM, between about 260 RPM and about 400 RPM, between about 260 RPM and about 380 RPM, between about 260 RPM and about 360 RPM, between about 260 RPM and about 340 RPM, between about 260 RPM and about 320 RPM, between about 260 RPM and about 300 RPM, between about 260 RPM and about 280 RPM, between about 280 RPM and about 500 RPM, between about 280 RPM and about 480 RPM, between about 280 RPM and about 460 RPM, between about 280 RPM and about 440 RPM, between about 280 RPM and about 420 RPM, between about 280 RPM and about 400 RPM, between about 280 RPM and about 380 RPM, between about 280 RPM and about 360 RPM, between about 280 RPM and about 340 RPM, between about 280 RPM and about 280 RPM, between about 300 RPM and about 500 RPM, between about 380 RPM and about 480 RPM, between about 380 RPM and about 460 RPM, between about 380 RPM and about 440 RPM, between about 380 RPM and about 420 RPM, between about 380 RPM and about 400 RPM, between about 400 RPM and about 500 RPM, between about 400 RPM and about 480 RPM, between about 400 RPM and about 460 RPM, between about 400 RPM and about 440 RPM, or between about 400 RPM and about 420 RPM. The agitation can be performed continuously or periodically.

Temperature

The culturing step described herein can be performed at a temperature of 32° C. to about 39° C., about 32° C. to about 37° C., between about 32° C. and about 37.5° C., between about 34° C. and about 37° C., or between about 35° C. and about 37° C. For example, the mammalian cells can be incubated at a temperature of about 37° C. from the beginning to the end of the first period of time. Skilled practitioners will appreciate that the temperature can be changed or may vary slightly during the first period of time, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, or fifteen days after the start of the first period of time, or at any time point within the first period of time. For example, the temperature can be shifted upwards by about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0° C. In another example, the temperature can be shifted downwards by about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C.

$CO_2$

The culturing step can be performed using an atmosphere containing about 1% to 15% $CO_2$, at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$. Methods for sparging CO2 into a production bioreactor are well known in the art.

Any of the methods described herein can also include culturing the cells during the first time period in a humidified atmosphere comprising at least or about 20%, 30%, 40%, 50%, 60%, 70%, 85%, 80%, 85%, 90%, or at least or about 95% humidity, or about 100% humidity.

$dO_2$

The culturing step can be performed by maintaining a dissolved oxygen ($dO_2$) in the cell culture of between about 3% and about 55%, between about 3% and about 50%, between about 3% and about 45%, between about 3% and about 40%, between about 3% and about 35%, between about 3% and about 30%, between about 3% and about 25%, between about 3% and about 20%, between about 3% and about 15%, between about 5% and about 55%, between about 5% and about 50%, between about 5% and about 45%, between about 5% and about 40%, between about 5% and about 35%, between about 5% and about 30%, between about 5% and about 25%, between about 5% and about 20%, between about 5% and about 15%, between about 5% and about 10%, between about 10% and about 55%, between about 10% and about 50%, between about 10% and about 45%, between about 10% and about 40%, between about 10% and about 35%, between about 10% and about 30%, between about 10% and about 25%, between about 10% and about 20%, between about 15% and about 55%, between about 15% and about 50%, between about 15% and about 45%, between about 15% and about 40%, between about 15% and about 35%, between about 15% and about 30%, between about 15% and about 25%, between about 15% and about 20%, between about 20% and about 55%, between about 20% and about 50%, between about 20% and about 45%, between about 20% and about 40%, between about 20% and about 35%, between about 20% and about 30%, between about 20% and about 25%, between about 25% and about 55%, between about 25% and about 50%, between about 25% and about 45%, between about 25% and about 40%, between about 25% and about 35%, between about 25% and about 30%, between about 30% and about 55%, between about 30% and about 50%, between about 30% and about 45%, between about 30% and about 40%, between about 30% and about 35%, between about 35% and about 55%, between about 35% and about 50%, between about 35% and about 45%, between about 35% and about 40%, between about 40% and about 55%, between about 40% and about 50%, between about 40% and about 45%, between about 45% and about 55%, between about 45% and about 50%, or between about 50% and about 55%.

Recombinant Proteins

Non-limiting examples of recombinant proteins in any of the methods described herein are immunoglobulins, including light and heavy chain immunoglobulins, antibodies, including humanized antibodies that bind specifically to human complement protein C5, such as eculizumab, or antibody fragments, enzymes, such as α-galactosidase, Myozyme, Cerezyme, non-antibody proteins, such as human erythropoietin, tumor necrosis factor (TNF), interferon alpha or beta, or immunogenic or antigenic proteins or protein fragments for use in a vaccine. In some embodiments, the recombinant protein is an engineered protein that contains at least one multifunctional recombinant protein scaffold. See, for example, the recombinant antigen-binding proteins described in Gebauer et al., Current Opin. Chem. Biol. 13:245-255, 2009; and U.S. Patent Application Publication No. 2012/0164066. Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of therapeutic antibodies that can be produced by the methods described herein are known in the art.

Eculizumab can include a heavy chain including or consisting of SEQ ID NO: 1 and light chain including or consisting of SEQ ID NO: 2. Nucleic acid that encodes the heavy and light chains of eculizumab are known in the art (see, for example, the nucleic acid sequences in U.S. Pat. No. 6,355,245 and Fc region sequences in An et al., *mAbs* 1:6, 572-579, 2009).

Methods of Shifting the Isoelectric Profile of a Protein Product

The methods provided herein also include a step of incubating the product under conditions sufficient to shift the isoelectric profile of the product toward a more acidic profile for a second period of time, or incubating the product under conditions sufficient to shift the isoelectric profile of the product toward a more basic profile for a second period of time. Non-limiting aspects of this incubating step are described herein.

Recombinant Protein Product Incubated

The recombinant protein product incubated during the second period of time can be a mixture of the recombinant protein and the mammalian cells in culture. In some embodiments, the methods further include a step of clarifying the culture through some form of filtration. The recombinant protein product incubated during the second period of time may also be the recombinant protein in a clarified tissue culture medium. In some embodiments, the methods further include a step of purifying the recombinant protein prior to the incubation for the second period of time and the recombinant protein product incubated during the second period of time is the purified protein product in a diluent. The diluent may be a buffer, such as phosphate buffered saline.

Vessels Used for Incubation

In any of the examples described herein, the recombinant protein product can be incubated in the production bioreactor (e.g., any of the exemplary production bioreactors described herein) or in a storage vessel. A storage vessel can be equipped to incubate the recombinant protein product under conditions sufficient to shift (e.g., an acidic or basic shift) the isoelectric profile of the recombinant protein product. For example, the storage vessel can be equipped to regulate one or more of the dO$_2$ level, the temperature, pH, and CO$_2$ level of the recombinant protein product (in any form described herein). The storage vessel can also be, e.g., equipped to regulate the agitation of the recombinant protein product. The storage vessel can have a volume of, e.g., between about 20 L and about 5,000 L between about 20 L and about 4,000 L, between about 20 L and about 2,000 L, between about 20 L and about 1,000 L, between about 20 L and about 800 L, between about 20 L and about 600 L, between about 20 L and about 400 L, between about 20 L and about 200 L, between about 20 L and about 100 L, between about 50 L and about 5,000 L, between about 50 L and about 4,000 L, between about 50 L and about 2,000 L, between about 50 L and about 1,000 L, between about 50 L and about 800 L, between about 50 L and about 600 L, between about 50 L and about 400 L, between about 50 L and about 200 L, between about 50 L and about 100 L, between about 100 L and about 5,000 L, between about 100 L and about 4,000 L, between about 100 L and about 2,000 L, between about 100 L and about 1,000 L, between about 100 L and about 800 L, between about 100 L and about 600 L, between about 100 L and about 400 L, between about 100 L and about 200 L, between about 200 L and about 5,000 L, between about 200 L and about 4,000 L, between about 200 L and about 2,000 L, between about 200 L and about 1,000 L, between about 200 L and about 800 L, between about 200 L and about 600 L, between about 200 L and about 400 L, between about 500 L and about 5,000 L, between about 500 L and about 4,000 L, between about 500 L and about 2,000 L, between about 500 L and about 1,000 L, between about 500 L and about 800 L, between about 1,000 L and about 5,000 L, between about 1,000 L and about 4,000 L, or between about 1,000 L and about 2,000 L.

Second Time Period

In any of the examples described herein, the second time period can be at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, at least 49 hours, at least 50 hours, at least 55 hours, at least 60 hours, at least 65 hours, at least 70 hours, at least 75 hours, at least 80 hours, at least 85 hours, at least 90 hours, at least 95 hours, at least 100 hours, at least 105 hours, at least 110 hours, at least 115 hours, at least 120 hours, at least 125 hours, at least 130 hours, at least 135 hours, at least 140 hours, at least 145 hours, at least 150 hours, at least 155 hours, at least 160 hours, at least 165 hours, at least 170 hours, at least 175 hours, at least 180 hours, at least 185 hours, at least 190 hours, at least 195 hours, or at least 200 hours after the critical time period of the culture.

In the methods for shifting the protein product to a more basic isoelectric profile described herein, the second time period can be at least 2 hours (e.g., at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, at least 49 hours, at least 50 hours, at least 55 hours, at least 60 hours, at least 65 hours, at least 70 hours, at least 75 hours, at least 80 hours, at least 85 hours, at least 90 hours, at least 95 hours, at least 100 hours, at least 105 hours, at least 110 hours, at least 115 hours, at least 120 hours, at least 125 hours, at least 130 hours, at least 135 hours, at least 140 hours, at least 145 hours, at least 150 hours, at least 155 hours, at least 160 hours, at least 165 hours, at least 170 hours, at least 175 hours, at least 180 hours, at least 185 hours, at least 190 hours, at least 195 hours, or at least 200 hours into the decline phase of the culture (e.g., at least 2 hours starting at the beginning of the decline phase).

In any of the examples described herein (e.g., methods for shifting the protein product to a more acidic isoelectric profile), the second time period can be between about 2 hours to about 200 hours, between about 2 hours and about 180 hours, between about 2 hours and about 160 hours, between about 2 hours and about 140 hours, between about 2 hours and about 120 hours, between about 2 hours and about 100 hours, between about 2 hours and about 80 hours, between about 2 hours and about 60 hours, between about 2 hours and about 40 hours, between about 2 hours and about 20 hours, between about 4 hours and about 200 hours, between about 4 hours and about 180 hours, between about 4 hours and about 160 hours, between about 4 hours and about 140 hours, between about 4 hours and about 120 hours, between about 4 hours and about 100 hours, between about 4 hours and about 80 hours, between about 4 hours and about 60 hours, between about 4 hours and about 40 hours, between about 4 hours and about 20 hours, between about 6 hours and about 200 hours, between about 6 hours and about 180 hours, between about 6 hours and about 160 hours, between about 6 hours and about 140 hours, between about 6 hours and about 120 hours, between about 6 hours and about 100 hours, between about 6 hours and about 80 hours, between about 6 hours and about 60 hours, between about 6 hours and about 40 hours, between about 6 hours and about 20 hours, between about 8 hours and about 200 hours, between about 8 hours and about 180 hours, between about 8 hours and about 160 hours, between about 8 hours and about 140 hours, between about 8 hours and about 120 hours, between about 8 hours and about 100 hours, between about 8 hours and about 80 hours, between about 8 hours and about 60 hours, between about 8 hours and about 40 hours, between about 8 hours and about 20 hours, between about 10 hours and about 200 hours, between about 10 hours and about 180 hours, between about 10 hours and about 160 hours, between about 10 hours and about 140 hours, between about 10 hours and about 120 hours, between about 10 hours and about 100 hours, between about 10 hours and about 80 hours, between about 10 hours and about 60 hours, between about 10 hours and about 40 hours, between about 10 hours and about 20 hours, between about 15 hours and about 200 hours, between about 15 hours and about 180 hours, between about 15 hours and about 160 hours, between about 15 hours and about 140 hours, between 15 hours and about 120 hours, between 15 hours and about 100 hours, between 15 hours and about 80 hours, between 15 hours and about 60 hours, between 15 hours and about 40 hours, between 15 hours and about 20 hours, between about 20 hours and about 200 hours, between about 20 hours and about 180 hours, between about 20 hours and about 160 hours, between about 20 hours and about 140 hours, between about 20 hours and about 120 hours, between about 20 hours and about 100 hours, between about 20 hours and about 80 hours, between about 20 hours and about 60 hours, between about 20 hours and about 40 hours, between about 25 hours and about 200 hours, between about 25 hours and about 180 hours, between about 25 hours and about 160 hours, between about 25 hours and about 140 hours, between about 25 hours and about 120 hours, between about 25 hours and about 100 hours, between about 25 hours and about 80 hours, between about 25 hours and about 60 hours, or between about 25 hours and about 40 hours, of a decline phase of the culture.

Conditions Sufficient to Shift the Isoelectric Profile of the Product Towards a More Acidic Profile Conditions sufficient to shift the isoelectric profile of a recombinant protein product toward a more acidic profile can include one or more of: a range of temperatures, a range of $dO_2$ values, a range of pH values, a range of rates of agitation, and the addition of one or more agents to a liquid containing the recombinant protein product (e.g., a cell culture medium containing cells and the recombinant protein, a clarified culture medium containing the recombinant protein, or buffer containing the recombinant protein). Examples of pH values that can shift the isoelectric profile of a recombinant protein product toward a more acidic profile during the second time period are between about pH 7.00 to about pH 7.30, between about pH 7.00 to about pH 7.25, between about pH 7.00 to about pH 7.20, between about pH 7.00 to about pH 7.15, between about pH 7.00 to about pH 7.10, between about pH 7.00 to about pH 7.05, between about pH 7.05 to about pH 7.30, between about pH 7.05 to about pH 7.25, between about pH 7.05 to about pH 7.20, between about pH 7.05 to about pH 7.15, between about pH 7.05 to about pH 7.10, between about pH 7.10 to about pH 7.30, between about pH 7.10 to about pH 7.25, between about pH 7.10 to about pH 7.20, between about pH 7.10 to about pH 7.15, between about pH 7.15 to about pH 7.30, between about pH 7.15 to about pH 7.25, between about pH 7.15 to about pH 7.20, between about pH 7.20 to about pH 7.30, between about pH 7.20 to about pH 7.25, or between about pH 7.25 to about pH 7.30.

Examples of $dO_2$ values that can shift the isoelectric profile of a recombinant protein product toward a more acidic profile during the second time period are between about 2% to about 35%, between about 2% to about 35%, between about 2% to about 30%, between about 2% to about 25%, between about 2% to about 20%, between about 2% to about 15%, between about 2% to about 10%, between about 2% to about 5%, between about 5% to about 35%, between about 5% to about 30%, between about 5% to about 25%, between about 5% to about 20%, between about 5% to about 15%, between about 5% to about 10%, between about 10% to about 35%, between about 10% to about 30%, between about 10% to about 25%, between about 10% to about 20%, between about 10% to about 15%, between about 15% to about 35%, between about 15% to about 30%, between about 15% to about 25%, between about 15% to about 20%, between about 20% to about 35%, between about 20% to about 30%, between about 20% to about 25%, between about 25% to about 35%, between about 25% to about 30%, or between about 30% to about 35%.

Examples of temperatures that can shift the isoelectric profile of a recombinant protein product toward a more acidic profile during the second time period are between about 30° C. to about 39° C., between about 30° C. to about 38° C., between about 30° C. to about 37.5° C., between about 30° C. to about 37° C., between about 30° C. to about 36° C., between about 30° C. to about 35° C., between about 30° C. to about 34° C., between about 30° C. to about 33° C., between about 30° C. to about 32° C., between about 31° C. to about 39° C., between about 31° C. to about 38° C., between about 31° C. to about 37.5° C., between about 31° C. to about 37° C., between about 31° C. to about 36° C., between about 31° C. to about 35° C., between about 31° C. to about 34° C., between about 31° C. to about 33° C., between about 32° C. to about 39° C., between about 32° C. to about 38° C., between about 32° C. to about 37.5° C., between about 32° C. to about 37° C., between about 32° C. to about 36° C., between about 32° C. to about 35° C., between about 32° C. to about 34° C., between about 33° C. to about 39° C., between about 33° C. to about 38° C., between about 33° C. to about 37.5° C., between about 33° C. to about 37° C., between about 33° C. to about 36° C., between about 33° C. to about 35° C., between about 34° C. to about 39° C., between about 34° C. to about 38° C., between about 34° C. to about 37.5° C., between about 34° C. to about 37° C., between about 34° C. to about 36° C., between about 35° C. to about 39° C., between about 35° C. to about 38° C., between about 35° C. to about 37.5° C., between about 35° C. to about 37° C., between about 36° C. to about 39° C., between about 36° C. to about 38° C., between about 36° C. to about 37.5° C., between about 37° C. and about 39° C., between about 37° C. to about 39° C., or between about 36° C. to about 37° C.

Examples of rates of agitation that can shift the isoelectric profile of a recombinant protein product toward a more acidic profile during the second time period are between about 200 RPM to about 400 RPM, between about 200 RPM to about 380 RPM, between about 200 RPM to about 360 RPM, between about 200 RPM to about 340 RPM, between about 200 RPM to about 320 RPM, between about 200 RPM to about 300 RPM, between about 200 RPM to about 280 RPM, between about 200 RPM to about 260 RPM, between about 200 RPM to about 240 RPM, between about 200 RPM to about 220 RPM, between about 220 RPM to about 400 RPM, between about 220 RPM to about 380 RPM, between about 220 RPM to about 360 RPM, between about 220 RPM to about 340 RPM, between about 220 RPM to about 320 RPM, between about 220 RPM to about 300 RPM, between 220 RPM to about 280 RPM, between about 220 RPM to about 260 RPM, between about 220 RPM to about 240 RPM, between about 240 RPM to about 400 RPM, between about 240 RPM to about 380 RPM, between about 240 RPM to about 360 RPM, between about 240 RPM to about 340 RPM, between about 240 RPM to about 320 RPM, between about 240 RPM to about 300 RPM, between about 240 RPM to about 280 RPM, between about 240 RPM to about 260 RPM, between about 260 RPM to about 400 RPM, between about 260 RPM to about 380 RPM, between about 260 RPM to about 360 RPM, between about 260 RPM to about 340 RPM, between about 260 RPM to about 320 RPM, between about 260 RPM to about 300 RPM, between about 260 RPM to about 280 RPM, between about 280 RPM to about 400 RPM, between about 280 RPM to about 380 RPM, between about 280 RPM to about 360 RPM, between about 280 RPM to about 340 RPM, between 280 RPM to about 320 RPM, between about 280 RPM to about 300 RPM, between about 300 RPM to about 400 RPM, between about 300 RPM to about 380 RPM, between about 300 RPM to about 360 RPM, between about 300 RPM to about 340 RPM, between about 300 RPM to about 320 RPM, between about 320 RPM to about 400 RPM, between about 320 RPM to about 380 RPM, between about 320 RPM to about 360 RPM, between about 320 RPM to about 340 RPM, between about 340 RPM to about 400 RPM, between about 340 RPM to about 380 RPM, between about 340 RPM and about 360 RPM, between about 360 RPM to about 400 RPM, between about 360 RPM to about 380 RPM, or between about 380 RPM to about 400 RPM.

Non-limiting examples of a condition that can induce an acidic shift in the isoelectric profile of a recombinant protein product during the second period of time include one or more of: an agitation rate of between about 200 RPM to about 280 RPM, between about 210 RPM to about 270 RPM, between about 220 RPM to about 260 RPM, between about 230 RPM to about 250 RPM, or about 240 RPM; a temperature of between about 31.5° C. and about 41.5° C., between about 32.5° C. and about 40.5° C., between about 33.5° C. and about 39.5° C., between about 34.5° C. and about 38.5° C., between about 35.5° C. and about 37.5° C., or about 36.5° C.; a pH of between about 7.10 and about 7.50 (e.g., between about 7.15 and about 7.45, between about 7.20 and about 7.40, between about 7.25 and about 7.35, or about 7.32; and a $dO_2$ value of between about 2% and about 35%, between about 2% and about 30%, between about 2% and about 25%, between about 2% and about 20%, between about 2% and about 15%, between about 2% and about 10%, between about 2% and about 7%, or about 5%.

Conditions Sufficient to Shift the Isoelectric Profile of the Product Towards a More Basic Profile Conditions sufficient to shift the isoelectric profile of a recombinant protein product toward a more basic profile can include one or more of: time, a range of specific temperatures, a range of specific $dO_2$ values, a range of specific pH values, a range of specific rates of agitation, and the addition of one or more agents (e.g., New Zealand bovine serum albumin) to a liquid containing the recombinant protein product (e.g., a cell culture medium containing cells and the recombinant protein, a clarified culture medium containing the recombinant protein, or buffer containing the recombinant protein). Any of the exemplary conditions used to produce the product for the first period of time can be used to shift the isoelectric profile to a more basic profile during the second period of time. Exemplary conditions that can be used to shift the isoelectric profile of a recombinant protein product to a more basic profile are provided below.

Examples of $dO_2$ values that can shift the isoelectric profile of a recombinant protein product toward a more basic profile during the second time period are, e.g., between about 35% to about 50%, between about 35% to about 45%, between about 35% to about 40%, between about 40% to about 50%, or between about 45% to about 50%.

Examples of pH values that can shift the isoelectric profile of a recombinant protein product toward a more basic profile during the second time period are, e.g., between about pH 6.70 to about pH 7.00, between about pH 6.70 to about pH 6.90, between about pH 6.70 to about pH 6.90, between about pH 6.70 to about pH 6.80, between about pH 6.80 to about pH 7.00, between pH 6.80 to about pH 6.90, or between about pH 6.90 to about pH 7.00.

A shift of the isoelectric profile of a recombinant protein product toward a more basic profile can be achieved, e.g., in part, by using a second period of time that is, between about 10 minutes and about 6 hours, between about 10 minutes and about 5.5 hours, between about 10 minutes and about 5.0 hours, between about 10 minutes and about 4.5 hours, between about 10 minutes and about 4.0 hours, between about 10 minutes and about 3.5 hours, between about 10 minutes and about 3.0 hours, between about 10 minutes and about 2.5 hours, between about 10 minutes and about 2.0 hours, between about 10 minutes and about 1.5 hours, between about 10 minutes and about 1.0 hour, or between about 10 minutes and about 0.5 hour, after the critical time period of the culture. A shift in the isoelectric profile of a recombinant protein product toward a more basic profile can be achieved, e.g., in part, by using a second period of time that is, e.g., between about 10 minutes to about 8 hours, between about 10 minutes to about 7.5 hours, between about 10 minutes to about 7.0 hours, between about 10 minutes to about 6.5 hours, between about 10 minutes to about 6.0 hours, between about 10 minutes to about 5.5 hours, between about 10 minutes to about 5.0 hours, between about 10 minutes to about 4.5 hours, between about 10 minutes to about 4.0 hours, between about 10 minutes to about 3.5 hours, between about 10 minutes to about 3.0 hours, between about 10 minutes to about 2.5 hours, between about 10 minutes to about 2.0 hours, between about 10 minutes to about 1 hour, or between about 10 minutes to about 0.5 hour of a decline phase of the culture (e.g., the second period of time starting at the beginning of the decline phase or at a selected time into the decline phase).

Achieved Shifts in Isoelectric Profile

Some embodiments include the use of a condition that produces a product having a basic profile. For example, use of a the raw material New Zealand bovine serum or New Zealand bovine serum albumin produces a product having a more basic isoelectric profile and the incubating shifts the product to a more acidic profile.

Some embodiments of the methods that include a step of incubating the recombinant protein product under conditions sufficient to shift the isoelectric profile of a recombinant protein toward a more acidic profile result in an increase in the level (or quantity) of at least one, two, three, or four of the more acidic protein subpopulation(s) in the profile and a decrease in the level (or quantity) of at least one, two, three, or four of the more basic protein subpopulations in the profile. In some embodiments, where the isoelectric profile comprises seven or eight protein subpopulations having an isoelectric point of between about 5.2 and about 6.7 (e.g., between about 5.45 and about 6.55), the method results in an increase in the level (or quantity) of at least two, three, four, or five of the more acidic protein subpopulations and a decrease in the level (or quantity) of at least two, three, or four of the more basic protein subpopulations.

Some embodiments of the methods that include a step of incubating the recombinant protein product under conditions sufficient to shift the isoelectric profile of a recombinant protein toward a more basic profile result in an increase in the level (or quantity) of at least one, two, three, or four of the more basic protein subpopulation(s) in the profile and/or a decrease in the level (or quantity) of at least one, two, three, or four of the more acidic protein subpopulation(s) in the profile.

In a particular example, when a recombinant protein product has seven protein subpopulations with an isoelectric point between about 5.45 and about 6.55 (e.g., eculizumab), the more acidic profile or the more basic profile comprises, consists, or consists essentially of the following: (1) a quantity of protein populating each of the second, third, and fourth most basic protein subpopulations of the seven protein subpopulations of ≥10% of the total mass of protein; (2) the quantity of protein populating each of the third and fourth most basic protein subpopulations of the seven protein subpopulations that is less than the quantity of protein populating the second most basic protein subpopulation of the seven protein subpopulations; (3) the quantity of protein populating the most acidic protein subpopulation is ≤3% of the total mass of protein; (4) the quantity of protein populating the second most acidic protein subpopulation is ≤6% of the total mass of protein; (5) the quantity of protein populating the third most acidic protein subpopulation is ≤9% of the total mass of protein; (6) the quantity of protein populating the most basic protein subpopulation is ≤8% of the total mass of protein; (7) there are no other minor protein subpopulations having a quantity of protein of ≤6% of the total mass of protein, other than the most acidic, the second most acidic, the third most acidic, and the most basic protein subpopulations of the seven protein subpopulations. In some embodiments, the incubation results in a recombinant protein product (e.g., eculizumab) having this more basic and/or more acidic profile.

Determining the Isoelectric Profile of the Recombinant Protein Product

Some embodiments further include one or more steps of assaying the product to determine the isoelectric profile. For example, a step of assaying the product to determine its isoelectric profile can be performed immediately following the end of the first period of time and before the incubating step. This is done to determine whether to incubate the product under conditions sufficient to shift the isoelectric profile of a recombinant protein product toward a more acidic profile during the second period of time or to determine whether to incubate the product under conditions sufficient to shift the isoelectric profile of a recombinant protein product toward a more basic profile during the second period of time.

Some embodiments further include a further step of assaying the product to determine the isoelectric profile immediately following the end of the second period of time to determine if additional shifting of the isoelectric protein product is necessary. For example, the assaying step immediately following the second period of time can be used to determine if a further incubating step, such as a repetition of an incubating step, is necessary to shift to a more acidic or a more basic profile. Such a decision can be made by comparing the determined isoelectric profile at the end of the second period of time to a reference profile (e.g., any of the reference profiles described herein or known in the art).

Purifying Recombinant Protein Product

As is known in the art, a recombinant protein product (e.g., a shifted recombinant protein product) can be purified using methods known in the art. For example, one or more steps of filtration and chromatography, such as affinity chromatography, protein A capture chromatography, anionic exchange chromatography, cation exchange chromatography, mixed mode resin chromatography, molecular sieve chromatography, and hydrophobic interaction chromatography can be used to purify the recombinant protein product, before or after shifting. Additional methods for purifying a recombinant protein product (e.g., a shifted recombinant protein product) are well known in the art.

The purified protein product (e.g., a shifted recombinant protein product) can then, optionally, be mixed or added to a pharmaceutically acceptable excipient to generate a drug substance. Examples of pharmaceutically acceptable excipients (e.g., non-naturally occurring pharmaceutically acceptable excipients) are well known in the art.

Recombinant Protein Products

Also provided are recombinant protein products produced by any of the methods described herein. For example, provided herein are recombinant protein products (e.g., eculizumab) produced by a method that includes: (a) culturing mammalian cells containing a nucleic acid encoding a recombinant protein in a production bioreactor under conditions sufficient to produce the product for a first period of time that consists of a growth phase and/or a stationary phase of the mammalian cells; (b) assaying the product at the end of the first period of time to the isoelectric profile; and (c) incubating the product under conditions sufficient to shift the isoelectric profile of the product toward a more acidic profile for a second period of time that consists of at least 6 hours of a decline phase of the mammalian cells, or incubating the product under conditions sufficient to shift the isoelectric profile of the product toward a more basic profile for a second period of time of a decline phase of the mammalian cells; and optionally, (d) assaying the product to determine the isoelectric profile and repeating step (c) if the isoelectric profile requires further shifting.

Also provided are recombinant protein products (e.g., eculizumab) produced by a method that includes: (a) culturing mammalian cells containing a nucleic acid encoding a recombinant protein in a production bioreactor under conditions sufficient to produce the product for a first period of time that comprises a growth phase of the mammalian cells and terminates at a critical time point; (b) incubating the product under conditions sufficient to shift the isoelectric profile of the product toward a more acidic profile for a second period of time that consists of at least 6 hours of a decline phase of the mammalian cells; and optionally (c) assaying the product to determine the isoelectric profile and repeating step (b) if the isoelectric profile requires further shifting toward a more acidic profile. Further provided are recombinant protein products (e.g., eculizumab) produced by a method that includes: (a) culturing mammalian cells containing a nucleic acid encoding a recombinant protein in a production bioreactor under conditions sufficient to produce the product for a first period of time that that comprises a growth phase of the mammalian cells and terminates at a critical time point; (b) incubating the product under conditions sufficient to shift the isoelectric profile of the product toward a more basic profile for a second period of time of a decline phase of the mammalian cells; and optionally (c) assaying the product to determine the isoelectric profile and repeating step (b) if the isoelectric profile requires further shifting toward a more basic profile.

Non-limiting aspects of the methods used to produce the recombinant protein products described herein are described above, and can be used in any combination without limitation.

EXAMPLES

The invention is further described in the following examples, which do not limit the scope of the invention described in the claims.

Example 1. Shifting of the Isoelectric Profile of Eculizumab

A set of experiments was performed to determine if the isoelectric profile of eculizumab could be shifted by continuing incubation of a cell culture in a 10,000 L bioreactor. In these experiments, culture samples were taken daily and the recombinant eculizumab purified using a protein A affinity chromatography. The isoelectric profile of the resulting purified eculizumab was determined using isoelectric focusing. The methods and materials used in these experiments are described below.

Materials

The materials used for these experiments include: clarified bioreactor samples from a culture of mammalian cells containing a nucleic acid that encodes eculizumab, and Protein A Sepharose columns.

Methods

A 10,000 L production bioreactor was seeded with mammalian cells containing a nucleic acid encoding eculizumab. At 5-15 days post inoculation, the 10,000 L bioreactor cell culture was sampled on days 5, 6, 7, 8, 9, 10, 11, 12, 13, 14, and 15 in a first experiment and a second experiment. Each sample was clarified by centrifugation and 0.22 μm filtration, and stored at 2-8° C. Next, each clarified sample was filtered a second time and passed through a Protein A column, to purify eculizumab. Isoelectric profiling was then performed on the purified eculizumab samples.

Results

Figure 2:
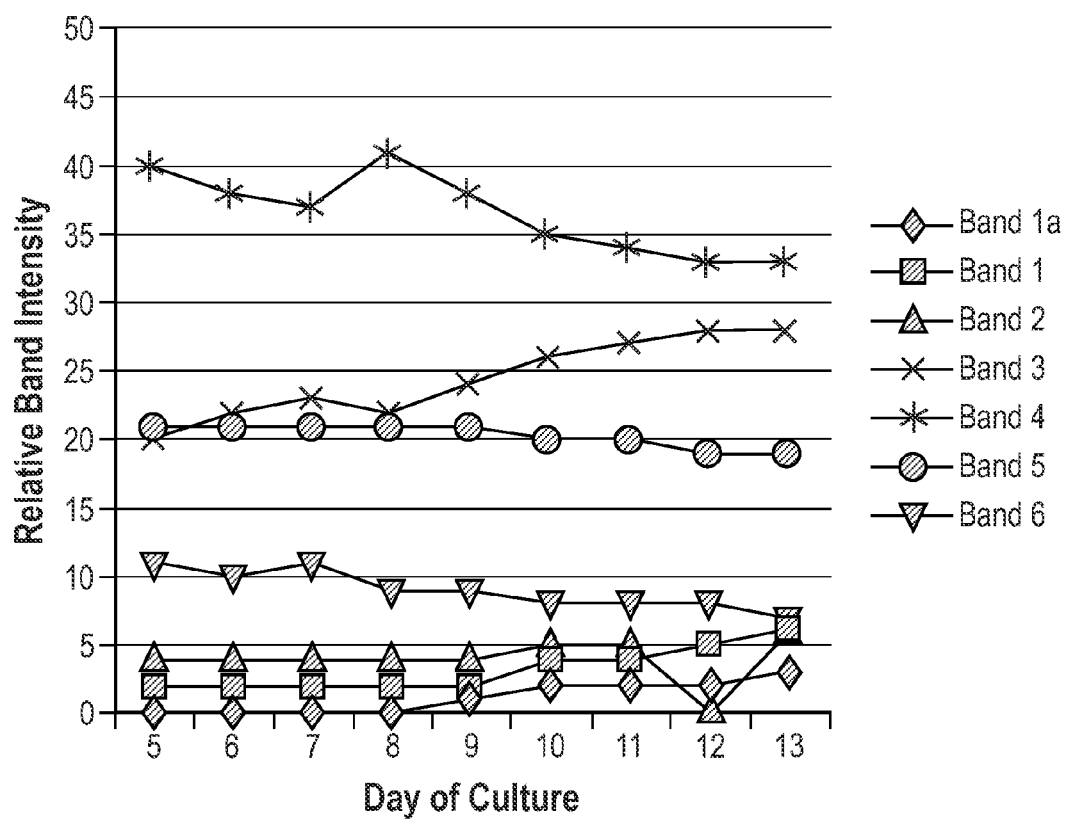
FIG. 2 is another graph showing the percentage of band intensity for each band in the isoelectric profile of eculizumab produced by a first fed batch culture run performed in a 10,000-L bioreactor from day 5 to day 13.
Figure 3:
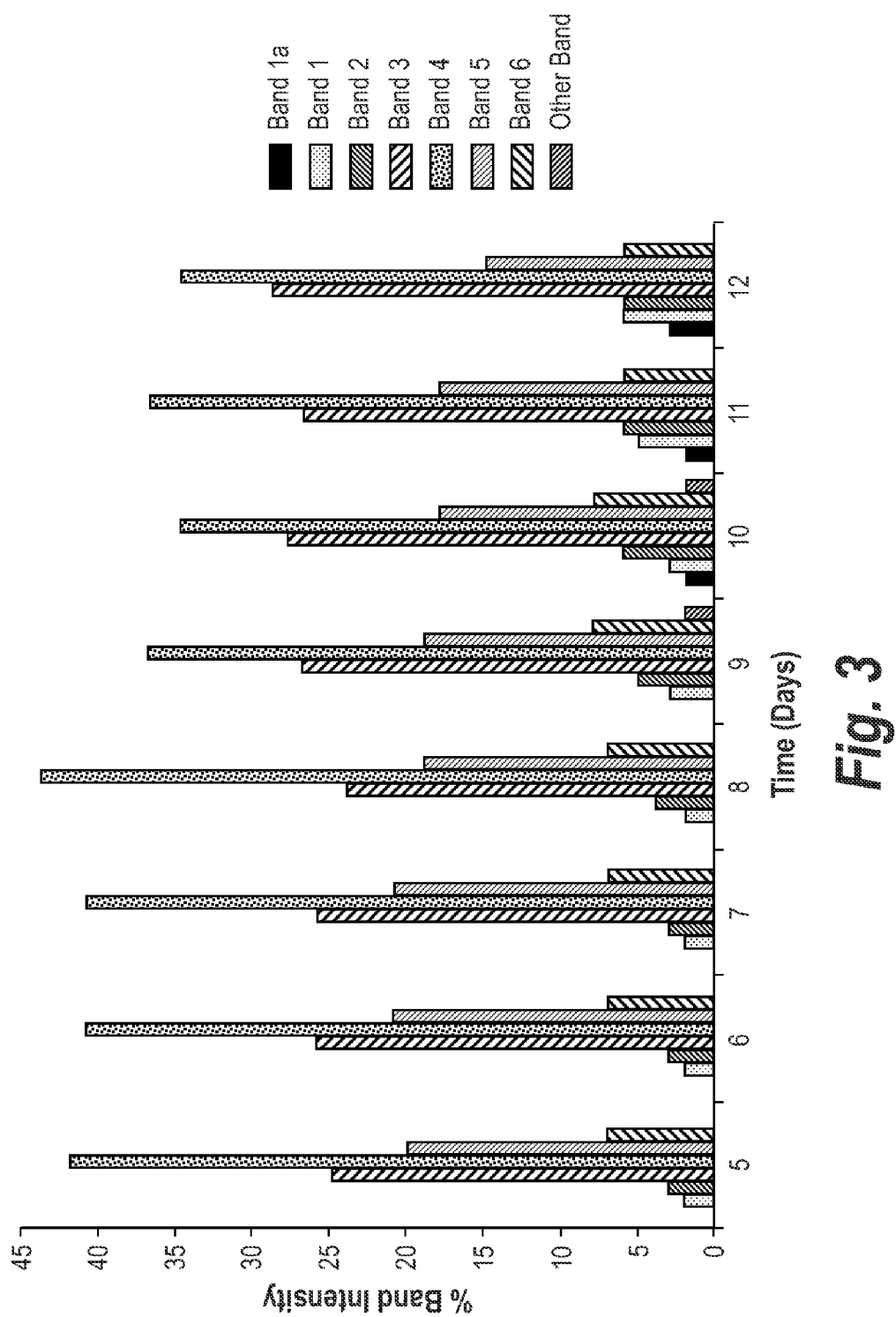
FIG. 3 is a graph of the percentage of band intensity for each band in the isoelectric profile of eculizumab produced by a second fed batch culture run performed using a 10,000-L bioreactor from day 5 to day 12.
Figure 4:
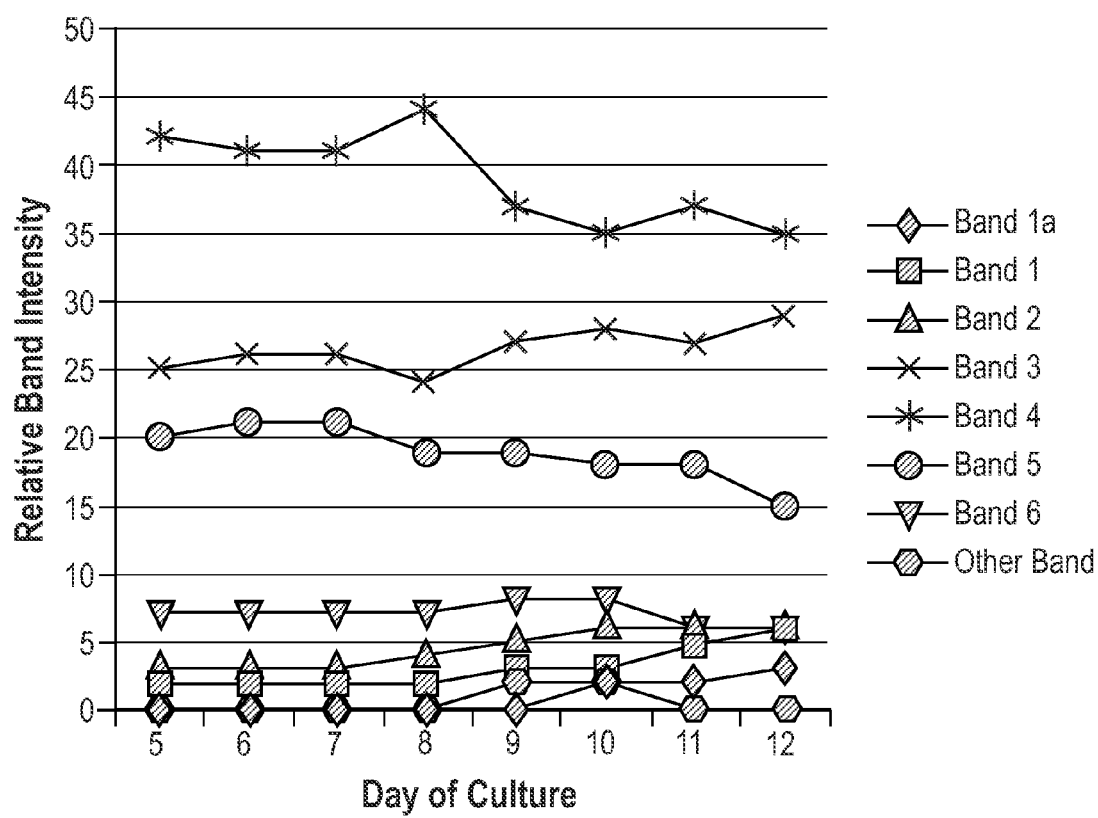
FIG. 4 is another graph of the percentage of band intensity for each band in the isoelectric profile of eculizumab produced by a second fed batch culture run performed using a 10,000-L bioreactor from day 5 to day 12.

Tables 1 and 2 summarize the data collected in the first and second 10,000 L cell cultures, respectively, on the relative amounts of the isoelectric protein bands 1a, 1, 2, 3, 4, 5, and 6. The bands were numbered in order from most acidic to most basic as determined using isoelectric focusing gel electrophoresis on each sample obtained from cell cultures over days 5-13. The critical time point in these 10,000 L fed batch cell cultures was determined to be time point at which the viable cell density decreases in the decline phase to reach a viable cell density of ~15×10$^5$ cells/mL. The data in Tables 1 and 2 demonstrate that continuing to culture the mammalian cells past the critical time point of the culture could produce an acidic shift in the isoelectric profile of eculizumab in the culture. Graphical representations of the data from the first 10,000 L bioreactor cell culture are shown in FIGS. 1 and 2, and graphical representations of the data from the second 10,000 L bioreactor cell culture are shown in FIGS. 3 and 4.

The data shown in FIGS. 1-4 also demonstrate that as you continue to culture the mammalian cells past the critical time point of the culture, the distribution of eculizumab molecules corresponding to different but discreet bands within the isoelectric profiles in the culture shifts from a more basic isoelectric profile to a more acidic isoelectric profile. In the first 10,000 L cell culture, there was an increase in the level (or quantity) of the acidic bands 1a (0% to 2%), 1 (2% to 6%), 2 (4% to 5%), and 3 (20% to 29%) observed between day 5 and day 13 of the culture. This shifting of material into the acidic bands in the first cell culture was mirrored by a decrease in the quantities of the basic bands 4 (40% to 32%), 5 (21% to 19%), 6 (11% to 7%) between day 5 and day 13 of the culture. One band more basic than band 6 disappeared completely after 10 days. The data in the second 10,000 L cell culture displayed a similar shifting of material within the isoelectric profile of eculizumab over time.

The data in this example demonstrate that continuing to incubate the culture for a second period of time that goes beyond the critical time point of the culture or extends the duration of the decline phase of the culture produces a redistribution of material within the isoelectric profile or an "acidic shift" in the isoelectric profile of eculizumab in the culture.

TABLE 1

First Experiment: Isoelectric Profile of Eculizumab over Time

| | Day 5 | Day 6 | Day 7 | Day 8 | Day 9 | Day 10 | Day 11 | Day 12 | Day 13 |
|---|---|---|---|---|---|---|---|---|---|
| QC-ID | 0311-0270 | 0311-0271 | 0311-0272 | 0311-0387 | 0311-0388 | 0311-0456 | 0311-0457 | 0311-0458 | 0311-0459 |
| Band 1a | ND | ND | ND | ND | 1 | 2 | 2 | 2 | 3 |
| Band 1 | 2 | 2 | 2 | 2 | 2 | 4 | 4 | 5 | 6 |
| Band 2 | 4 | 4 | 4 | 4 | 4 | 5 | 5 | 6 | 6 |
| Band 3 | 20 | 22 | 23 | 22 | 24 | 26 | 27 | 28 | 28 |
| Band 4 | 40 | 38 | 37 | 41 | 38 | 35 | 34 | 33 | 33 |
| Band 5 | 21 | 21 | 21 | 21 | 21 | 20 | 20 | 19 | 19 |
| Band 6 | 11 | 10 | 11 | 9 | 9 | 8 | 8 | 8 | 7 |
| other | 2 | 3 | 2 | 1 | 2 | ND | ND | ND | ND |
| pI range | 5.64-6.39 | 5.64-6.38 | 5.64-6.38 | 5.64-6.64 | 5.57-6.65 | 5.56-6.33 | 5.57-6.32 | 5.57-6.32 | 5.56-6.38 |

TABLE 2

Second Experiment: Isoelectric Profile of Eculizumab over Time

| | Day 5 | Day 6 | Day 7 | Day 8 | Day 9 | Day 10 | Day 11 | Day 12 |
|---|---|---|---|---|---|---|---|---|
| QC-ID | 0411-0063 | 0411-0064 | 0411-0065 | 0411-0066 | 0411-0067 | 0411-0068 | 0411-0069 | 0411-0146 |
| Band 1a | ND | ND | ND | ND | ND | 2 | 2 | 3 |
| Band 1 | 2 | 2 | 2 | 2 | 3 | 3 | 5 | 6 |
| Band 2 | 3 | 3 | 3 | 4 | 5 | 6 | 6 | 6 |
| Band 3 | 25 | 26 | 26 | 24 | 27 | 28 | 27 | 29 |
| Band 4 | 42 | 41 | 41 | 44 | 37 | 35 | 37 | 35 |
| Band 5 | 20 | 21 | 21 | 19 | 19 | 18 | 18 | 15 |
| Band 6 | 7 | 7 | 7 | 7 | 8 | 8 | 6 | 6 |
| other | ND | ND | ND | ND | 2 | 2 | ND | ND |
| pI range | 5.64-6.35 | 5.62-6.33 | 5.64-6.33 | 5.63-6.32 | 5.63-6.61 | 5.55-6.60 | 5.56-6.19 | 5.55-6.25 |

Example 2. Effect of pH and $dO_2$ on Shift in Isoelectric Profile of Eculizumab Next, we sought to evaluate the effects of pH and $dO_2$ on the resulting isoelectric profile of a recombinant protein produced by the cell culture. For these small-scale cell cultures, NS0 mammalian cells containing a nucleic acid encoding eculizumab were cultured in 2-L fed-batch bioreactors.

Methods

A set of ten 2-L small-scale fed batch bioreactors were inoculated with NS0 mammalian cells containing a nucleic acid encoding eculizumab in a working volume of 1.3 L and cultured for a total of 16 days. The bioreactors were cultured at an agitation rate of 240 RPM at a controlled temperature of 36.5° C. The sparge air flow rate began at 3 sL/hr and increased to 9 sL/hr before additional oxygen was supplemented in order to maintain the specific $dO_2$ set point for the experimental condition. The cell cultures were run in duplicates at the five different experimental conditions listed below (conditions 1-5). Each bioreactor was run with a pH dead band set point of 0.02 (e.g., 7.32±0.02). The conditions were as follows:

(1) pH 7.0 and $dO_2$ of 15% (Control Conditions) (Cell Culture Runs 1 and 2);
(2) pH 7.32 and $dO_2$ of 5% (Cell Culture Runs 3 and 4);
(3) pH 7.32 and $dO_2$ of 50% (Cell Culture Runs 5 and 6);
(4) pH 6.95 and a $dO_2$ of 5% (Cell Culture Runs 7 and 8); and
(5) pH 6.95 and $dO_2$ of 50% (Cell Culture Runs 9 and 10).

Each of the 2-L bioreactor cultures was inoculated with an initial viable cell density of $3.5 \times 10^5$ cells/mL. Each of the inoculation cell sources for the bioreactors was derived from the same cell bank. Two duplicate spinner cultures, grown from a seed train process, were used to inoculate the bioreactors. The bioreactors in Cell Culture Runs 1, 7, and 8 were inoculated from a first spinner culture, and the bioreactors in Cell Culture Runs 2, 3, 4, 5, 6, 9, and 10 were inoculated from the second spinner culture. The generation number of the cells on day zero of the 10 2-L bioreactor cultures was approximately 77.3.

Process defined feeds were added to each 2-L culture upon the initiation of the feed criteria. The feed criteria was designated as when the cell culture reached a viable cell density$\geq 14 \times 10^5$). Upon reaching the feed criteria two different liquid culture medium were introduced into the bioreactors by sterile syringes and sidearm septums. Both liquid feeds for all of the 2-L bioreactors were 4% of the total tank volume. The liquid feeds were 52-mL and were distributed (fed) over 133 hours. The method of feed addition was performed using daily bolus feed shots of 9.4 mL of each liquid culture medium during the first five days, and a final 5.0 mL aliquot on the sixth and final day of feeding. New Zealand sourced BSA was used in all the culture media and feeding solutions.

In order to evaluate the resulting isoelectric profiles, 75 mL samples were removed from each 2-L bioreactor on the following schedule: samples were obtained on day 10, day 12, and day 14 for Cell Culture Runs 1, 3, and 5, and samples were obtained on day 5, day 8, and day 10 for Cell Culture Runs 2, 4, 6, 7, 8, 9, and 10. For Cell Culture Runs 2, 4, 6, 7, 8, 9, and 10, the final harvest samples were used for protein A purification of eculizumab and subsequent isoelectric focusing assays were performed on day 14. For Cell Culture Runs 1, 3, and 5, the final harvest samples were taken on day 16. A clarified sample of culture medium was prepared from each cell culture and eculizumab was purified and stored at 2° C. to 8° C. The stored samples of eculizumab containing culture medium were subsequently purified by protein A chromatography and the isoelectric profile was determined.

Results

Figure 5:
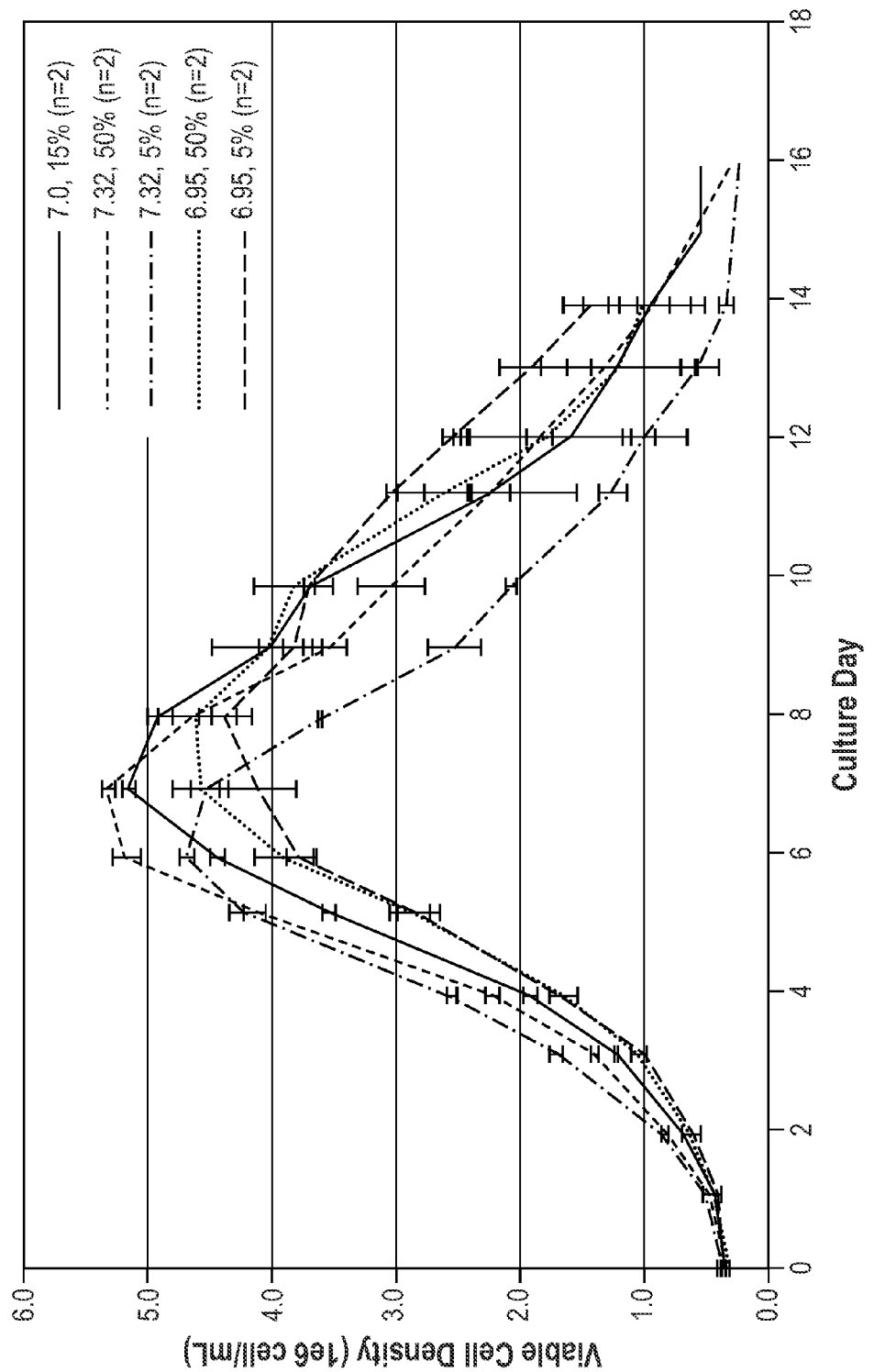
FIG. 5 is a graph of the viable cell density over time in fed batch culture runs performed using a 2-L bioreactor and one of the following combinations of pH and $dO_2$: pH 7.0 and $dO_2$ of 15%; pH 7.32 and $dO_2$ of 50%; pH 7.32 and $dO_2$ of 5%; pH 6.95 and $dO_2$ of 50%; and pH 6.95 and $dO_2$ of 5%. The mean data (n=2) are shown.

Cell growth in the five sets of bioreactor cell culture conditions was determined. See FIG. 5. The initial seeding density for all the 2-L bioreactors was consistent. The four bioreactors with a pH of 7.32 grew faster initially. The was not surprising because the optimal pH for growth in the culture media was 7.30. However, these four bioreactors had cell cultures which entered the decline phase more rapidly than the bioreactors under control conditions or the bioreactors set at pH 6.95. The cell cultures set at pH 6.95 and pH 7.32 and a $dO_2$ set point of 5% did not achieve the same integrated viable cell concentration (IVCC) as their 50% dissolved oxygen counterparts. This suggested that oxygen was limiting in these cultures. The control conditions of pH 7.0 and $dO_2$ of 15% was between the high and low pH conditions (pH 7.32 and pH of 6.95, respectively), indicating that even a slight pH modification below pH 7 can have a significant impact upon cell growth.

Productivity of the five different bioreactor conditions was determined. See FIG. 6. Significant differences in the specific productivity were observed amongst the five different tested pH/$dO_2$ conditions. Running the bioreactors at a pH set point of 7.32 at either high or low oxygen has a marked impact on specific productivity. The pH 7.32 bioreactor run at high oxygen (50%) achieved a higher integrated viable cell concentration and a higher final titer as compared to its 5% $dO_2$ counterpart. The bioreactors run at pH 6.95±0.02 had a higher specific productivity and was similar in productivity to the 2 L bioreactors run under control conditions. Therefore, at pH 6.95, the $dO_2$ set point differential (5% vs. 50%) did not have as much of an impact on specific productivity or final titer as compared to impact of $dO_2$ at pH 7.32. The bioreactors run at control conditions of pH 7.0 and 15% $dO_2$ produced the highest cumulative integrated viable cell concentration. The bioreactors run at control conditions also outperformed the bioreactor cell cultures run at pH 7.32 and 50% $dO_2$. The bioreactors run at control conditions produced eculizumab at 1600 mg/L, over 400 mg/L higher bioreactors run at the non-control conditions.

The evolution of the isoelectric profile of the antibody produced under the five sets of cell culture conditions was determined. See FIGS. 7 through 10. These data show how the quantity of material populating particular protein bands in the isoelectric profile for eculizumab change over culture duration including as it approaches and surpasses the critical time point of the culture. These data also show that there is an interaction between pH and $dO_2$ that appears to affect the isoelectric profile of eculizumab. A general trend is that as the culture duration increases past the critical time point and into the decline phase of the culture the quantity of material within acidic protein bands (e.g., bands 1, 2, and 3) in the isoelectric profile also increases. Correspondingly, the quantity of material populating basic protein bands (e.g., bands 5 and 6) decreases. Surprisingly, the data also show that low $dO_2$ set points result in an increased level (or quantity) of acidic protein bands in the isoelectric profile, while higher $dO_2$ set points increase the appearance and levels (or quantities) of basic protein bands in the isoelectric profile.

Figure 11:
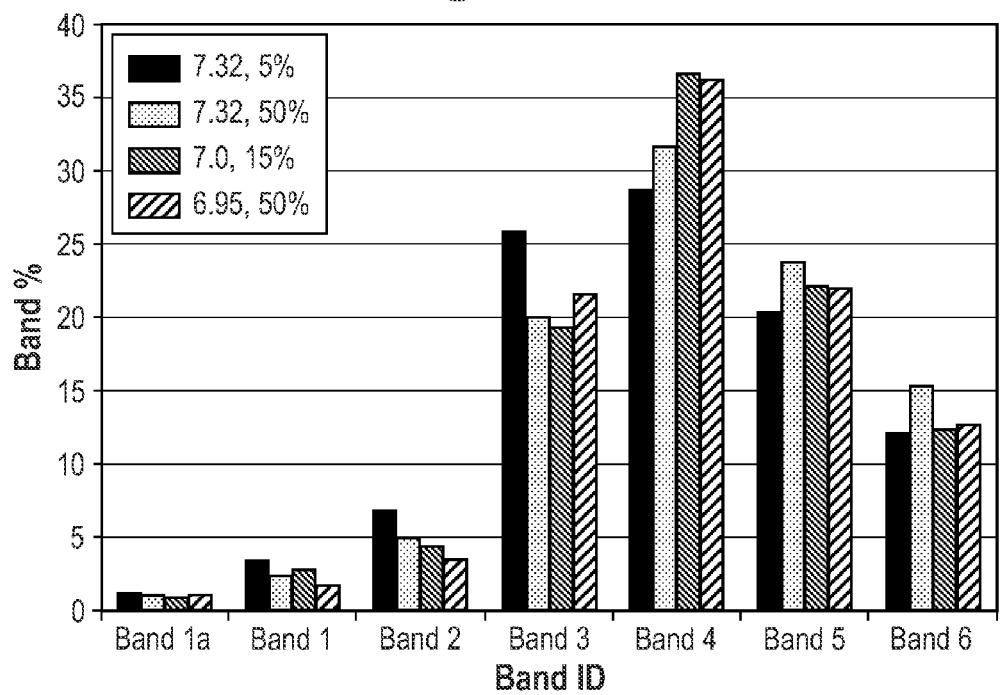
FIG. 11 is a graph showing the percentage of band intensity for each protein band in an isoelectric profile of eculizumab harvested from a fed batch culture runs performed using a 2-L bioreactor and one of the following combinations of pH and $dO_2$: pH of 7.32 and $dO_2$ of 5%, pH of 7.32 and a $dO_2$ of 50%, pH of 7.0 and a $dO_2$ of 15%, and pH of 6.95 and $dO_2$ of 50%, on day 14 of each culture, respectively.

FIG. 11 shows the levels (or quantities) of different protein bands in an isoelectric profile of eculizumab harvested at day 14 from four of the tested bioreactor cultures. The data clearly show that low $dO_2$ generates higher levels (or quantities) of more acidic protein bands, specifically bands 1a, 1, 2, and 3, and a higher pH generates higher levels (or quantities) of more acidic protein bands, specifically, bands 1 and 2.

The data in this example show a shift to a more acidic isoelectric profile was produced for eculizumab when the cell culture was cultured for a time period that extends past the critical time point and well into the decline phase (e.g., in this example the decline phase of the cell culture begins around day 6 or 7). The critical time point in this example is when the cell culture declines below $15 \times 10^5$ cell/ml in the decline phase of growth.

Example 3. Effect of Cell Source and Raw Materials on Isoelectric Profile

A further set of experiments were performed in order to determine the effect of cell source and raw materials on the isoelectric profile of eculizumab produced by a mammalian cell culture. The materials and methods used to perform these experiments are described below.

Methods

Eight 2-L bioreactors were inoculated and incubated for a total of 18 days. The working volume of each bioreactor culture was 1.3 L. Each of the 2-L fed batch bioreactor cultures were agitated counter-clockwise at 240 RPM at a thermocoupled temperature of 36.5° C. The sparge flow rate began at 3 sl/hour and ramped up to 9 sl/hour before oxygen supplementation was used to maintain the $dO_2$ set point at 15%. The bioreactor cultures were run at a pH of 7.0 with a dead band of ±0.02. Four of the 2-L fed batch bioreactor cultures were run with Cell Source A, and four of the 2-L fed batch bioreactor cultures were run with Cell Source B. Two of the 2-L fed batch bioreactor cultures, one from each cell source, were cultured using a first set of raw culture medium materials, the other six 2-L bed batch bioreactor cultures were cultured using a second set of raw culture medium materials: three replicates for each cell source. The exact set of experimental conditions tested are shown in Table 3. The eight bioreactors were inoculated with cells from a spinner culture (i.e., one spinner culture was prepared for each cell source). All eight of the 2-L fed batch bioreactor cultures were inoculated at a target seed density of $3.0 \times 10^5$ cells/mL.

In each of the bioreactor runs, the feeding of two liquid culture media into each bioreactor was initiated when the culture reached the feed criteria (viable cell density of $\geq 14 \times 10^5$ cells/mL) upon which a 1× bolus of a media supplement was introduced into each bioreactor via sterile syringe and sidearm septum. Both feeds for all 8 bioreactors were 4% of total tank volume each, or 52 mL of each of the liquid culture media added, distributed over 133 hours. The method of feed addition was done using daily bolus feed shots, with 9.4 mL of each feed during the first five days, and a final shot of 5.0 mL on the sixth and final day of feeding.

TABLE 3

Cell Source and Raw Material Combinations Tested

| Bioreactor Run ID # | D-10 Tank Position | Cell Source/Description of Bioreactor Condition |
|---|---|---|
| Cell Culture Run 11 | #1 | Cell Source A; First Set of Raw Materials |
| Cell Culture Run 12 | #2 | Cell Source B; First Set of Raw Materials |
| Cell Culture Run 13 | #3 | Cell Source B; Second Set of Raw Materials |
| Cell Culture Run 14 | #4 | Cell Source A; Second Set of Raw Materials |
| Cell Culture Run 15 | #5 | Cell Source A; Second Set of Raw Materials |
| Cell Culture Run 16 | #6 | Cell Source B; Second Set of Raw Materials |
| Cell Culture Run 17 | #7 | Cell Source B; Second Set of Raw Materials |
| Cell Culture Run 18 | #8 | Cell Source A; Second Set of Raw Materials |

Samples (75 mL) were harvested from each bioreactor as described below. For Cell Culture Runs 11 and 12, samples were taken on day 8, day 11, day 14, day 15, and day 16. For bioreactor runs 13 and 14, samples were taken on day 13, day 14, day 15, and day 16. The eculizumab present in each sample was purified using protein A chromatography, and the resulting purified protein was analyzed using isoelectric focusing electrophoresis.

Results

Figure 12:
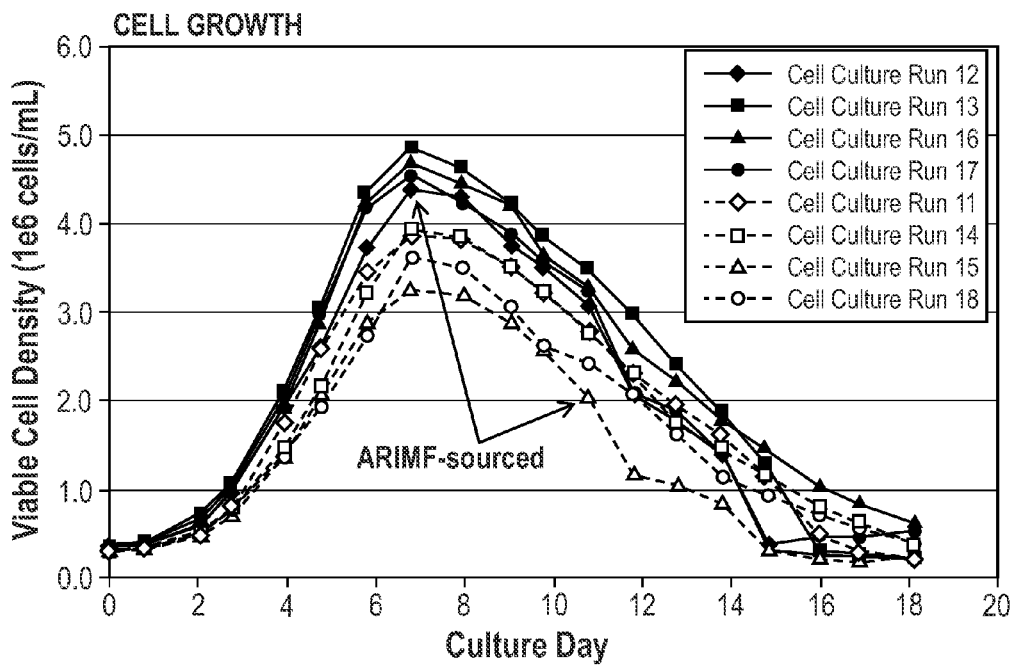
FIG. 12 is a graph showing the viable cell density over time in fed batch culture runs performed using a 2-L bioreactor and one of the following cell source and raw material combinations: Cell Source A and First Set of Raw Materials (Cell Culture Run 11); Cell Source B and First Set of Raw Materials (Cell Culture Run 12); Cell Source A and Second Set of Raw Materials (Cell Culture Runs 14 and 15); and Cell Source B and Second Set of Raw Materials (Cell Culture Runs 13, 16, 17, and 18).

Cell growth for the eight fed batch bioreactors is shown in FIG. 12. The initial seeding density for all eight bioreactors is consistent from vessel-to-vessel. The solid black lines show the data from cultures inoculated with Cell Source B, and the dashed black lines show the data from cultures inoculated with Cell Source A. The two subset runs that contained the First Set of Raw Materials are indicated by arrows for their respective cell source. The data show that cells derived from Cell Source B grew faster, reach a higher peak viable cell density (VCD), and decline in VCD slower than Cell Source A counterpart cultures. The cultures incubated with the First Set of Raw Materials are lower in cumulative viable cell density when compared to cultures incubated with the Second Set of Raw Materials. This can be easily seen in the Cell Culture Run 11 data.

Figure 13:
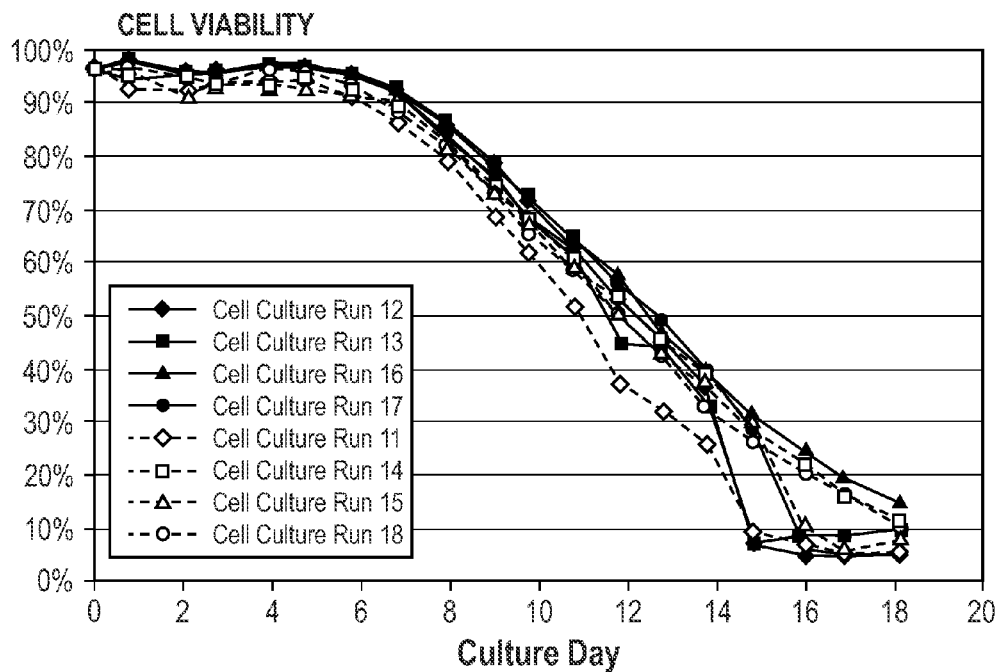
FIG. 13 is a graph showing the percentage cell viability over time in fed batch culture runs performed using a 2-L bioreactor and one of the following cell source and raw material combinations: Cell Source A and First Set of Raw Materials (Cell Culture Run 11); Cell Source B and First Set of Raw Materials (Cell Culture Run 12); Cell Source A and Second Set of Raw Materials (Cell Culture Runs 14 and 15); and Cell Source B and Second Set of Raw Materials (Cell Culture Runs 13, 16, 17, and 18).

The percentage of viable cells present in the culture over time in each bioreactor culture is shown in FIG. 13. The data between Cell Source A and Cell Source B look similar, with Cell Culture Run 11 having the lowest percentage viable cell density over time. The bioreactors containing Cell Source B seem to have a slightly higher percentage of viable cells between day 0 to day 14.

Figure 14:
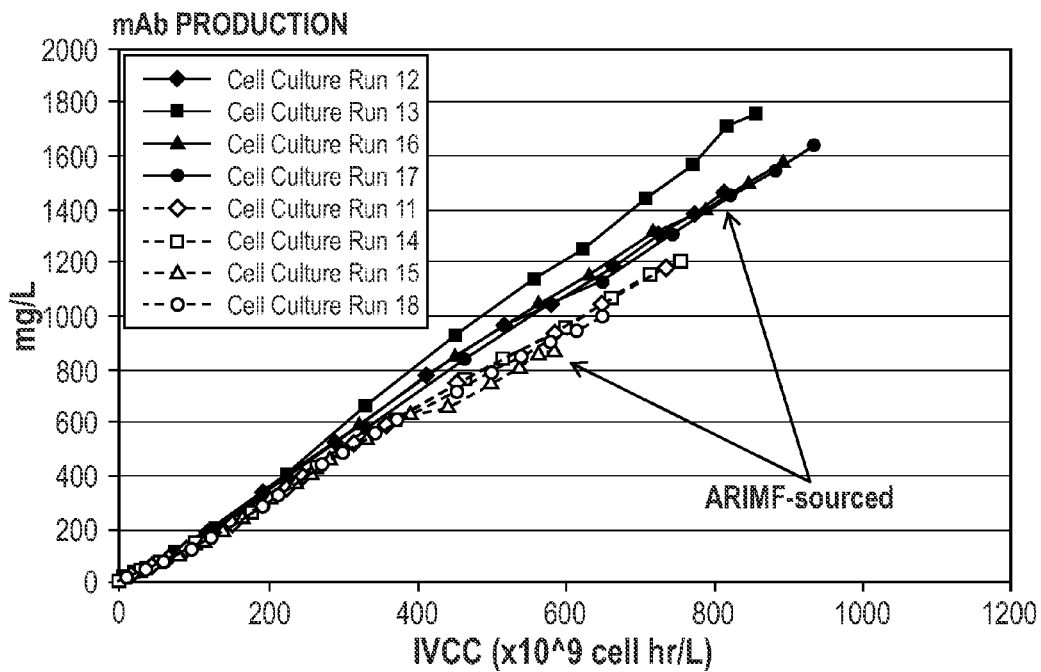
FIG. 14 is a graph showing the productivity (mg eculizumab/L as compared to the integrated viable cell concentration) in fed batch culture runs performed using a 2-L bioreactor and one of the following cell source and raw material combinations: Cell Source A and First Set of Raw Materials (Cell Culture Run 11); Cell Source B and First Set of Raw Materials (Cell Culture Run 12); Cell Source A and Second Set of Raw Materials (Cell Culture Runs 14 and 15); and Cell Source B and Second Set of Raw Materials (Cell Culture Runs 13, 16, 17, and 18).
Figure 15:
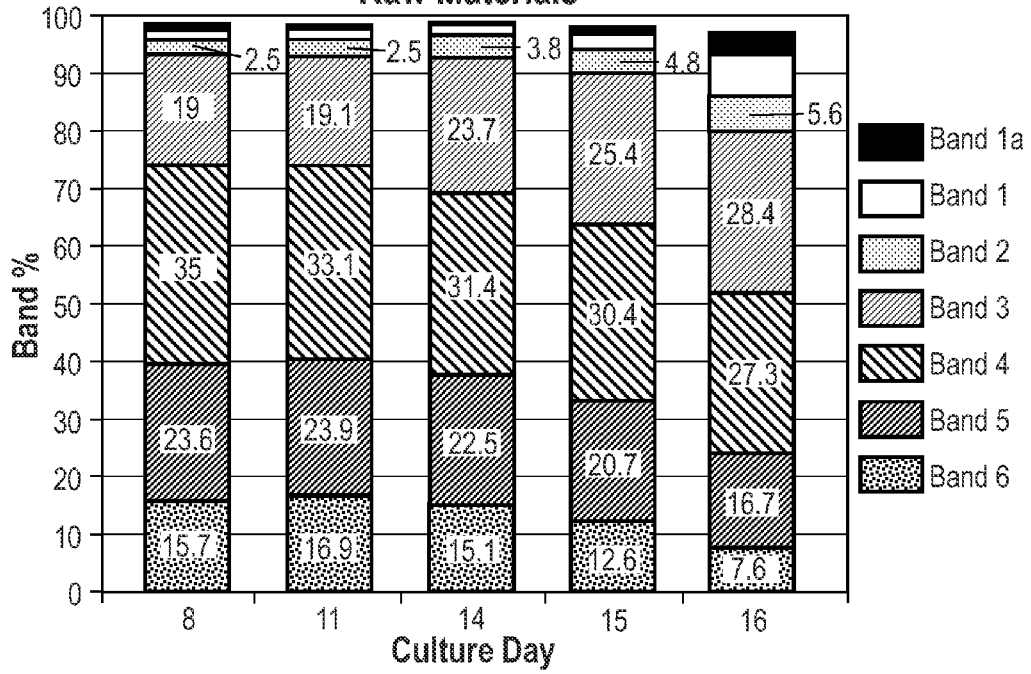
FIG. 15 is a graph showing the percentage of band intensity for each protein band in an isoelectric profile of eculizumab harvested from a fed batch culture run (Cell Culture Run 11) performed using a 2-L bioreactor, Cell Source A, and the First Set of Raw Materials on day 8, day 11, day 14, day 15, and day 16 of the culture.

The specific productivity of the eight bioreactor cultures is shown in FIG. 14. The cell source has an effect on productivity of the culture. The two cultures growth using the First Set of Raw Materials are indicated by arrows in FIG. 14. For each cell source used, the cell runs using the First Set of Raw Materials had lower specific productivity compared to their counterparts that use the Second Set of Raw Materials. The average titer of the four bioreactor cultures using Cell Source B was 1.64 grams/liter compared to only 1.11 grams/liter for the bioreactor cultures using Cell Source A. The bioreactor cultures using Cell Source B also were more productive on a per-cell basis (observed by the slope of the lines in FIG. 14).

FIGS. 15-18 display the time-course of the isoelectric profile of the eculizumab purified from the samples obtained from four of the eight different bioreactor cultures. The four cell culture runs used in these time course studies were Cell Culture Runs 11, 12, 13, and 14 (as shown in Table 4). The data in FIGS. 15-18 show that the changes in the isoelectric profile of eculizumab over the culture duration (as the culture is incubated for a further time period beyond the critical time period and/or incubated during the decline period of the culture). The data in FIGS. 15-18 show that the change in the isoelectric profile over time is the same for both the cultures using Cell Source A or Cell Source B. A general trend is noted that as the culture duration increases past the critical time point and into the decline growth phase, the levels (or quantities) of acidic protein bands (protein bands 1, 2, and 3) increase, while basic protein bands (protein bands 5 and 6) decrease. The data also indicate that a low $dO_2$ set point increases the levels (or quantities) of more acidic protein bands, while high $dO_2$ set point increases the appearance and frequency of more basic protein bands. The profiles from Cell Source A and Cell Source B that used the same raw materials look similar, while the profiles from the same cell source that use different raw materials are less similar. These data indicate that the raw materials used exhibit more of an impact on the isoelectric profile than the cell sources in these experiments. Both of the bioreactor cultures that used the First Set of Raw Materials met harvest criteria earlier than the cultures using the Second Set of Raw Materials.

Cell Culture Runs 11 and 12 met the following reference isoelectric profile on day 16: protein bands 3, 4, and 5≥10%; protein bands 3 and 4≥protein band 5; protein band 1a≤3%; protein band 1≤6%; protein band 2≤9%; protein band 6≤8%; no minor protein bands other than protein bands 1a, 1, 2, and 6; and all protein bands resolved between an isoelectric point of 5.45 and 6.55. Cell Culture Runs 11 and 12 met the reference isoelectric profile at 4 days past the critical time point (day 12) for Cell Culture Run 11 and 2 days past the critical time point (day 14) for Cell Culture Run 12. The critical time point used in these experiments was the time point when the viable cell density declines below $15 \times 10^5$ cells/mL. There is subtle overall shift in the isoelectric profile towards more basic protein bands across the board when the culturing utilizes new Zealand bovine serum components (e.g., bovine serum albumin).

In sum, these data demonstrate that continuing to incubate a culture for an additional time period (past the critical time period or into the decline phase of the culture) could produce a shift in the isoelectric profile of a recombinant protein product (e.g., such as eculizumab in the present examples).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of shifting the isoelectric profile of a recombinant protein product having seven protein subpopulations with an isoelectric point between about 5.45 and about 6.55, wherein the recombinant protein product is eculizumab and the method comprises:
   (a) fed batch culturing mammalian cells comprising a nucleic acid encoding a recombinant protein in a production bioreactor under conditions sufficient to produce the product for a first period of time that consists of a growth phase or a growth phase and a stationary phase of the mammalian cells or that comprises a growth phase of the mammalian cells and terminates at a critical time point; and
   (b) incubating the product under conditions sufficient to shift the isoelectric profile of the product toward a more acidic profile for a second period of time that consists of at least 6 hours of a decline phase of the mammalian cells, wherein the more acidic profile comprises an increase in the quantity of the fourth and fifth most acidic protein subpopulations of the seven protein subpopulations, and a decrease in the quantity of the first and second most basic protein subpopulations of the seven protein subpopulations, wherein the conditions sufficient to shift the isoelectric profile of the product towards a more acidic profile comprise (i) incubating in a dissolved oxygen ($dO_2$) concentration of between about 20% to about 45%; incubating in a medium having a pH of between about 7.0 and about 7.3; and/or (iii) incubating at a temperature of between about 30° C. and about 37.5° C.

2. The method of claim 1, further comprising assaying the product to determine the isoelectric profile and repeating step (b) if the the isoelectric profile requires further shifting toward the more acidic profile when compared to a reference isoelectric profile.

3. The method of claim 1, wherein the more acidic profile is an isoelectric profile, where:
   the quantity of protein populating each of the second, third, and fourth most basic protein subpopulations of the seven protein subpopulations is ≥10% of the total mass of protein in the profile;
   the quantity of protein populating each of the third and fourth most basic protein subpopulations of the seven protein subpopulations is less than the quantity of the second most basic protein subpopulation of the seven protein subpopulations;
   the quantity of protein populating the most acidic protein subpopulation of the seven protein subpopulations is ≤3% of the total mass of protein in the profile;
   the quantity of protein populating the second most acidic protein subpopulation of the seven protein subpopulations is ≤6% of the total mass of protein in the profile;
   the quantity of protein populating the third most acidic protein subpopulation of the seven protein subpopulations is ≤9% of the total mass of protein in the profile;
   the quantity of protein populating the most basic protein subpopulation of the seven protein subpopulations is ≤8% of the total mass of protein in the profile; and
   there are no other protein subpopulations having a quantity of protein of ≤6% of the total mass of protein, other than the most acidic, the second most acidic, the third most acidic, and the most basic protein subpopulations of the seven protein subpopulations.

4. The method of claim 1, wherein the $dO_2$ concentration is between about 20% to about 45%.

5. The method of claim 1, wherein the $dO_2$ concentration is between about 30% and about 35%.

6. The method of claim 2, wherein the assaying comprises isoelectric focusing electrophoresis.

7. The method of claim 6, wherein the isoelectric focusing electrophoresis is capillary electrophoresis or gel electrophoresis.

8. The method of claim 1, wherein the pH is between about 7.0 and about 7.25.

9. The method of claim 1, wherein the pH is between about between about 7.0 and about 7.20.

10. The method of claim 1, wherein the pH is between about 7.0 and about 7.15.

11. The method of claim 1, wherein the temperature is between about 33° C. and about 37.5° C.

12. The method of claim 1, wherein the conditions sufficient to shift the isoelectric profile of the product to a more acidic profile include incubating at an agitation rate of between about 200 RPM and about 400 RPM.

13. The method of claim 12, wherein the agitation rate is between about 220 RPM and about 350 RPM, or between about 220 RPM and about 300 RPM.

14. The method of claim 1, wherein eculizumab comprises a heavy chain comprising SEQ ID NO: 1 and light chain comprising SEQ ID NO: 2 or a heavy chain consisting of SEQ ID NO: 1 and a light chain consisting of SEQ ID NO: 2.

15. The method of claim 1, further comprising formulating the product into a pharmaceutical composition.

16. The method of claim 2, further comprising formulating the product into a pharmaceutical composition.

* * * * *

UNITED STATES PATENT AND TRADEMARK OFFICE
CERTIFICATE OF CORRECTION

| | |
|---|---|
| PATENT NO. | : 9,908,932 B2 |
| APPLICATION NO. | : 14/881799 |
| DATED | : March 6, 2018 |
| INVENTOR(S) | : Hunter F. Malanson et al. |

It is certified that error appears in the above-identified patent and that said Letters Patent is hereby corrected as shown below:

In the Drawings

Figure 16:
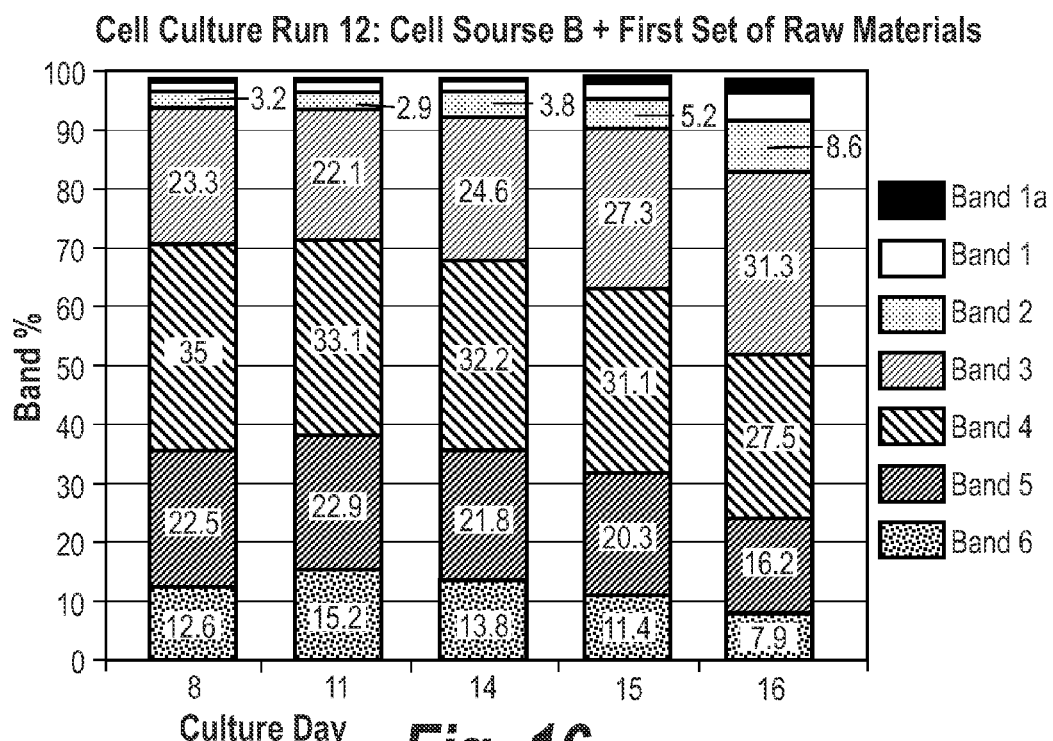
FIG. 16 is graph showing the percentage of band intensity for each protein band in an isoelectric profile of eculizumab harvested from a fed batch culture run (Cell Culture Run 12) performed using a 2-L bioreactor, Cell Source B, and the First Set of Raw Materials on day 8, day 11, day 14, day 15, and day 16 of the culture.

On sheet 11 of 12, in Figure 16, Line 1, delete "Sourse" and insert -- Source --, therefor.

Figure 17:
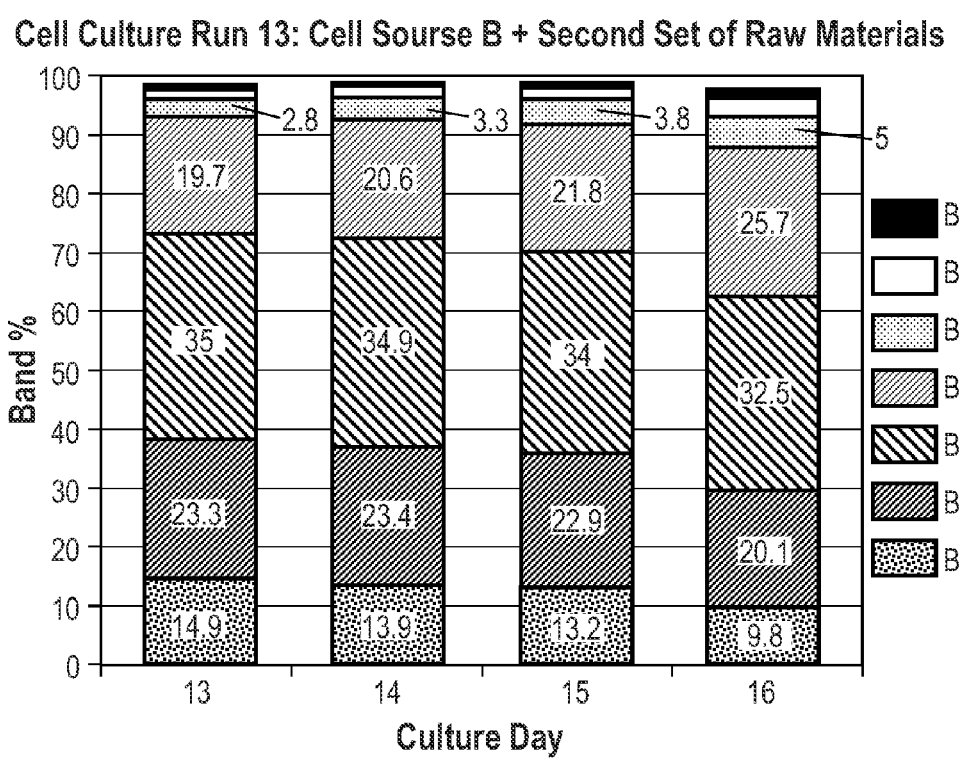
FIG. 17 is a graph showing the percentage of band intensity for each protein band in an isoelectric profile of eculizumab harvested from a fed batch culture run (Cell Culture Run 13) performed using a 2-L bioreactor, Cell Source B, and the Second Set of Raw Materials on day 13, day 14, day 15, and day 16 of the culture.

On sheet 11 of 12, in Figure 17, Line 1, delete "Sourse" and insert -- Source --, therefor.

Figure 18:
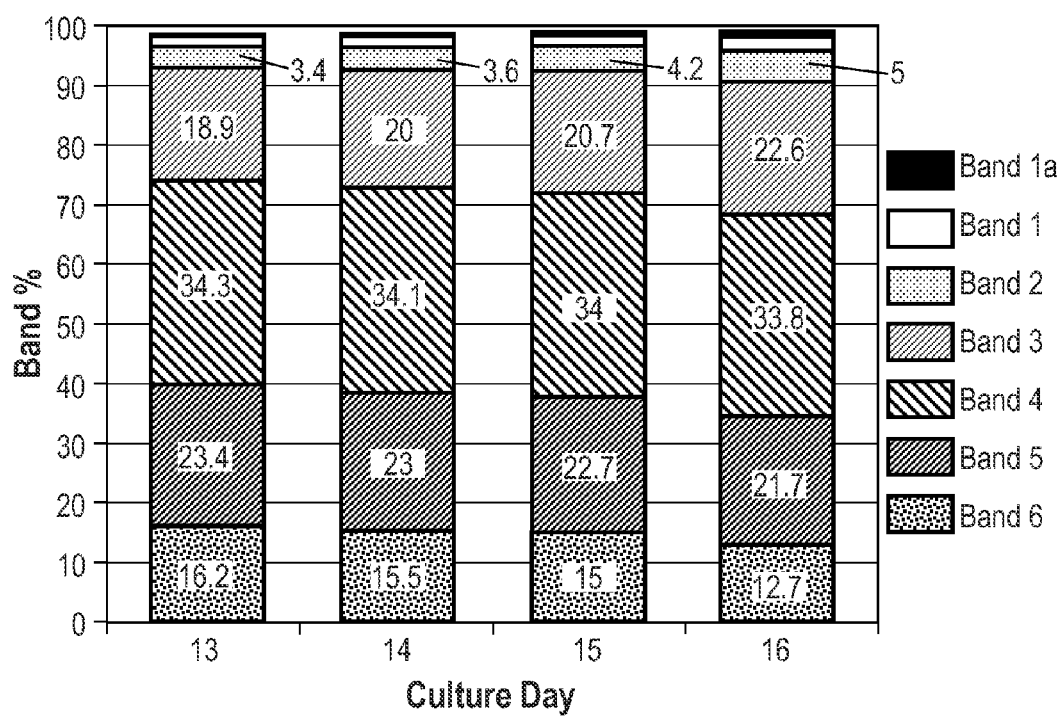
FIG. 18 is graph showing the percentage of band intensity for each protein band in an isoelectric profile of eculizumab harvested from a fed batch culture run (Cell Culture Run 14) performed using a 2-L bioreactor, Cell Source A, and the Second Set of Raw Materials on day 13, day 14, day 15, and day 16 of the culture.

On sheet 12 of 12, in Figure 18, Line 1, delete "Sourse" and insert -- Source --, therefor.

In the Specification

In Column 2, Line 36, delete "that that" and insert -- that --, therefor.

In Column 6, Line 10, delete "that that" and insert -- that --, therefor.

In Column 17, Line 6, delete "faction" and insert -- fraction --, therefor.

In Column 22, Line 5, delete "impellar." and insert -- impeller. --, therefor.

In Column 24, Lines 22-23, delete "alacizumab, alacizumab," and insert -- alacizumab, --, therefor.

In Column 24, Line 25, delete "basilizimab," and insert -- basiliximab, --, therefor.

In Column 24, Line 27, delete "densumab," and insert -- denosumab, --, therefor.

In Column 30, Line 37, delete "a the" and insert -- the --, therefor.

In Column 32, Line 44, delete "that that" and insert -- that --, therefor.

In Column 36, Line 9, delete "The" and insert -- This --, therefor.

Signed and Sealed this
Fifteenth Day of May, 2018

Andrei Iancu
*Director of the United States Patent and Trademark Office*

CERTIFICATE OF CORRECTION (continued)
U.S. Pat. No. 9,908,932 B2

Figure 6:
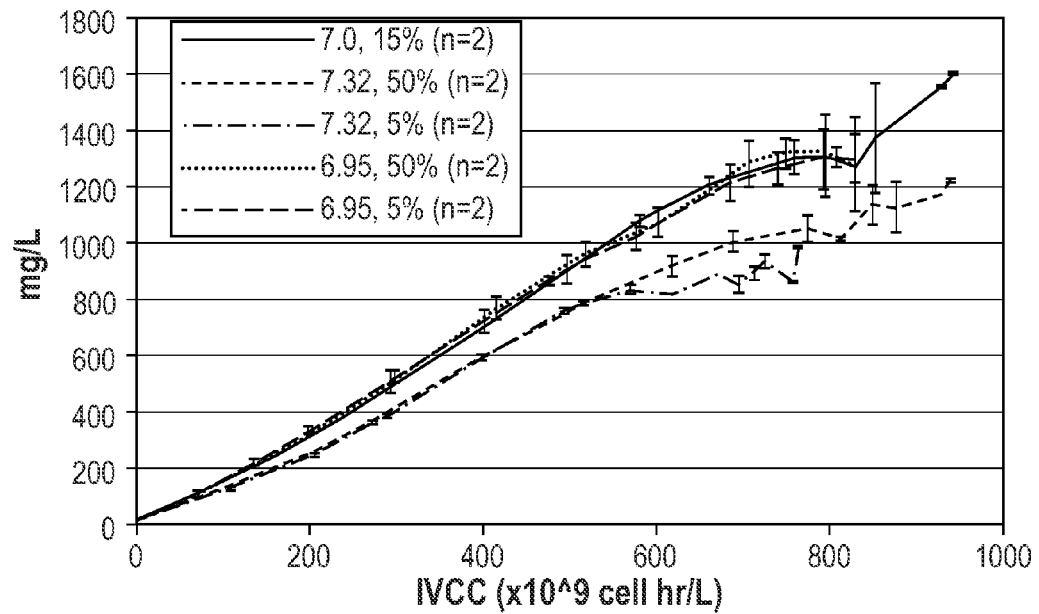
FIG. 6 is a graph comparing the mg/L eculizumab produced by a 2-L fed batch bioreactor cultures as compared to the integrated viable cell concentration in the same cultures. The different 2-L fed batch bioreactor culture runs were performed using a 2-L bioreactor and one of the following combinations of pH and $dO_2$: pH 7.0 and $dO_2$ of 15%; pH 7.32 and $dO_2$ of 50%; pH 7.32 and $dO_2$ of 5%; pH 6.95 and $dO_2$ of 50%; and pH 6.95 and $dO_2$ of 5%. The mean data (n=2) are shown.
Figure 7:
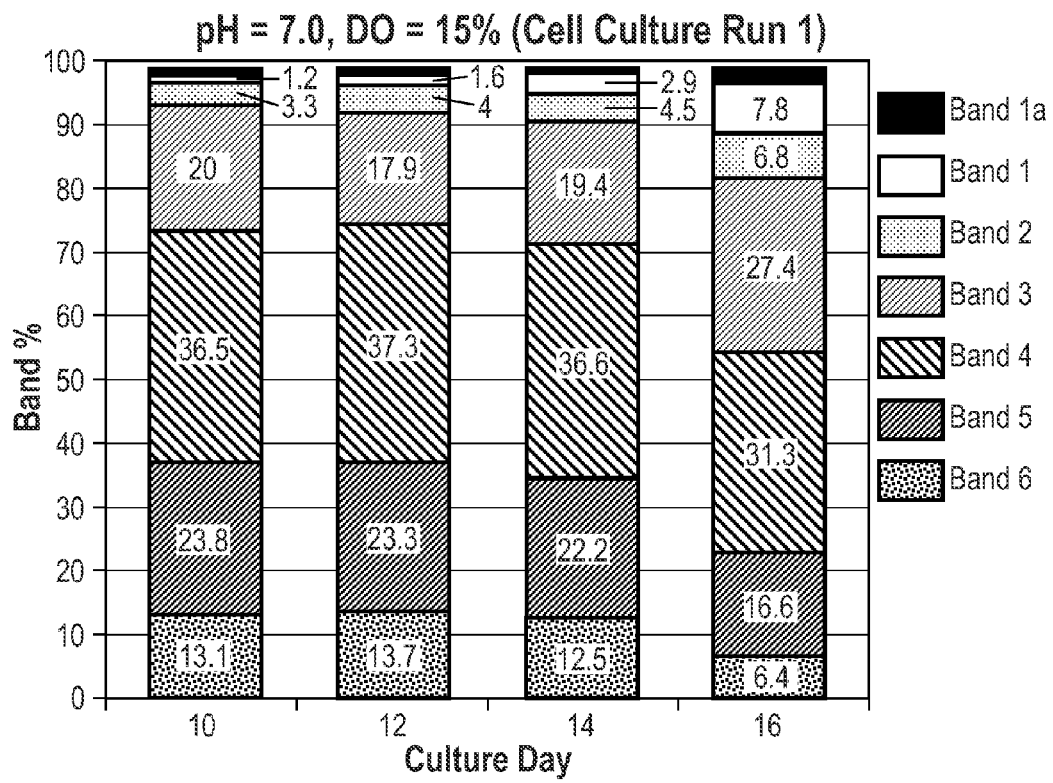
FIG. 7 is a graph showing the percentage of band intensity for each protein band in an isoelectric profile of eculizumab harvested from a fed batch culture run performed using a 2-L bioreactor, a pH of 7.0, and a $dO_2$ of 15% at day 10, day 12, day 14, and day 16 of the culture.
Figure 8:
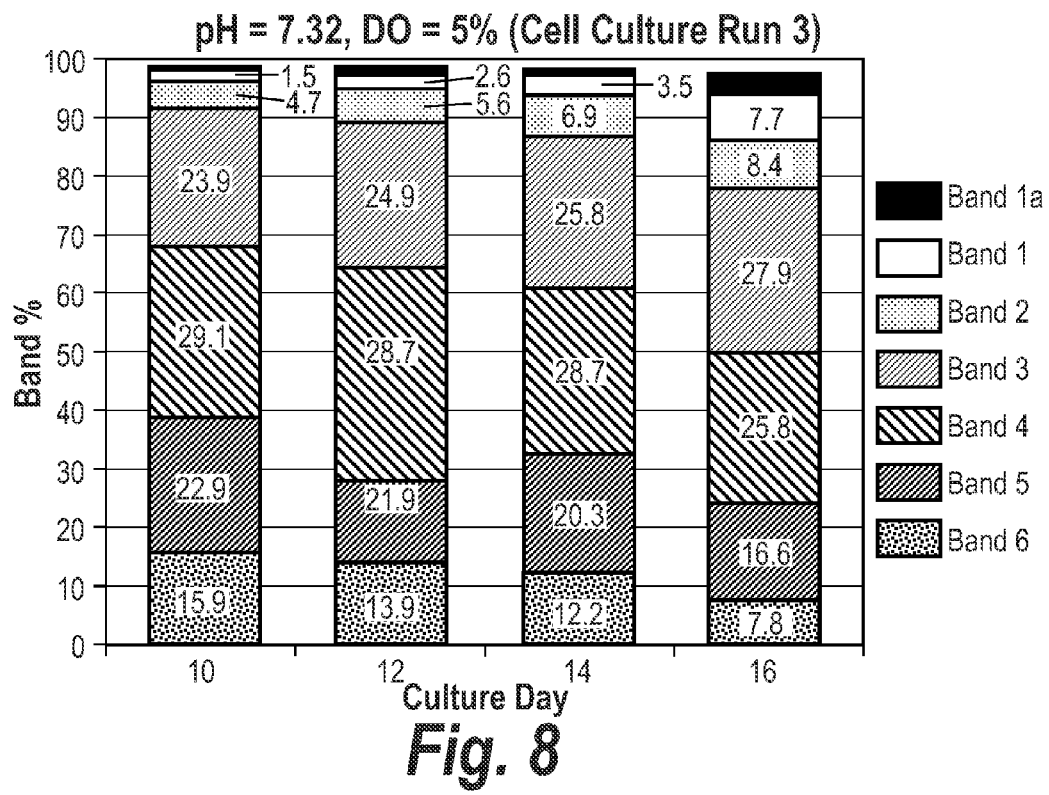
FIG. 8 is a graph showing the percentage of band intensity for each protein band in an isoelectric profile of eculizumab harvested from a fed batch culture run performed using a 2-L bioreactor, a pH of 7.32, and a $dO_2$ of 5% at day 10, day 12, day 14, and day 16 of the culture.
Figure 9:
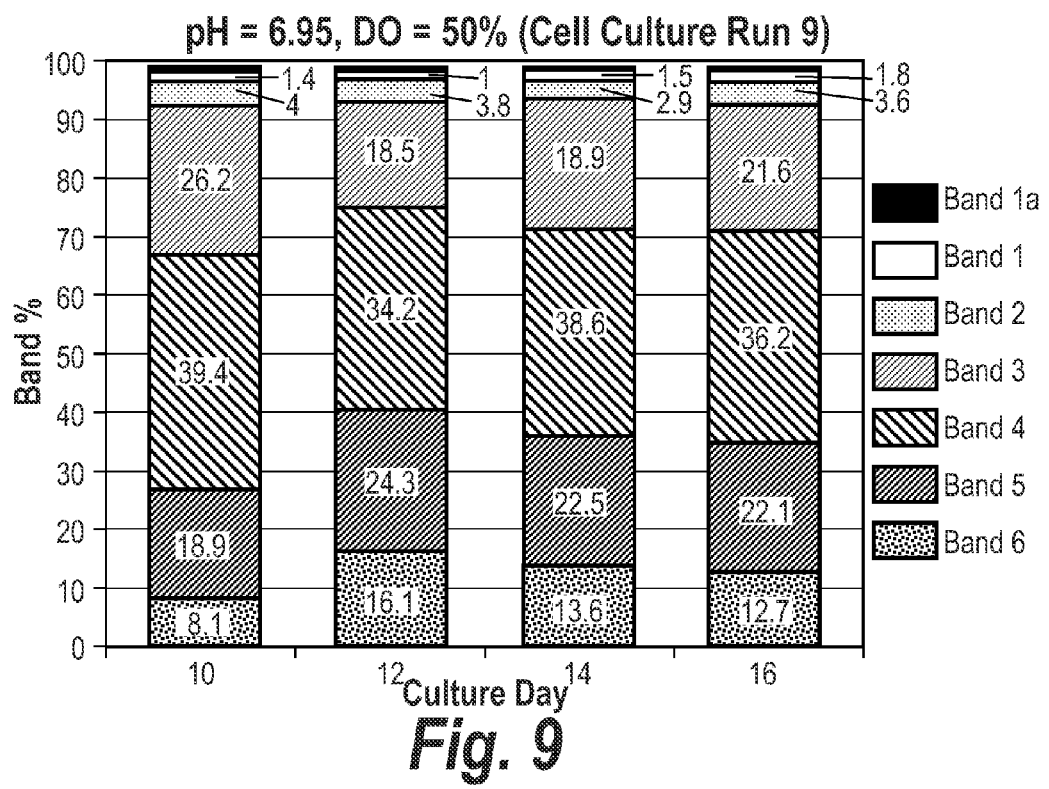
FIG. 9 is a graph showing the percentage of band intensity for each protein band in an isoelectric profile of eculizumab harvested from a fed batch culture run performed using a 2-L bioreactor, a pH of 6.95, and a $dO_2$ of 50% at day 5, day 8, day 10, and day 14 of the culture.
Figure 10:
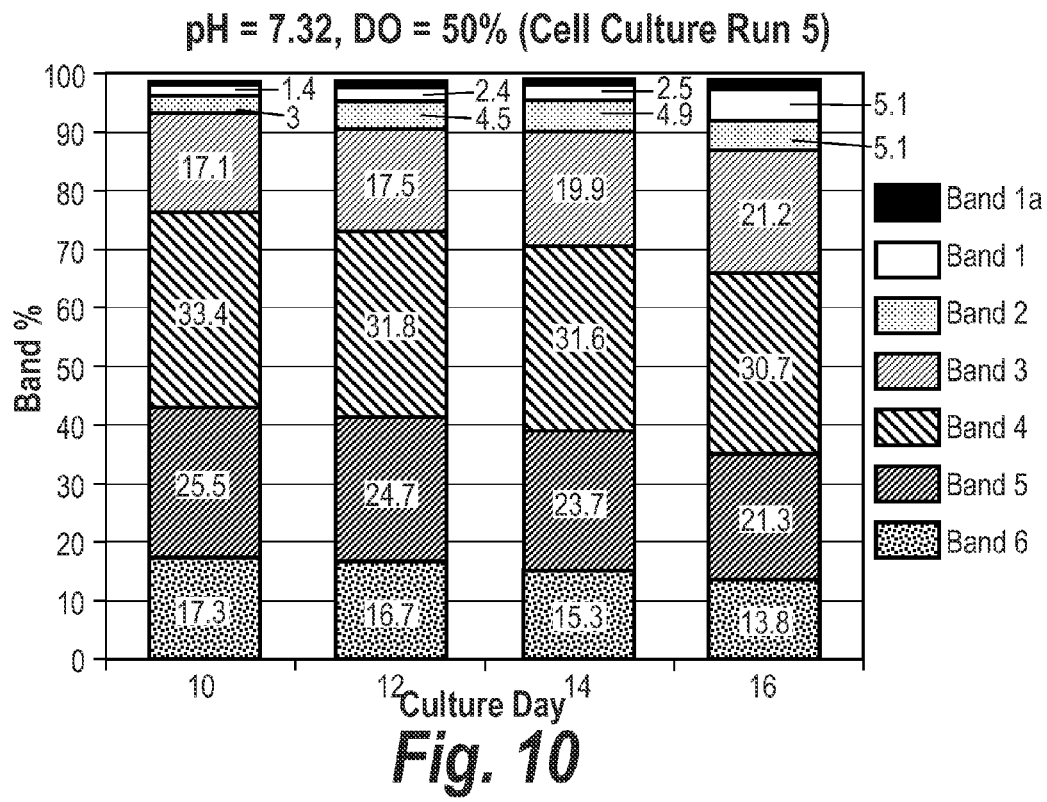
FIG. 10 is a graph showing the percentage of band intensity for each protein band in an isoelectric profile of eculizumab harvested from a fed batch culture run performed using a 2-L bioreactor, a pH of 7.32, and a $dO_2$ of 50% on day 10, day 12, day 14, and day 16 of the culture.

In Column 36, Lines 25-44, delete "FIG. 6. Significant differences in the specific productivity were observed amongst the five different tested pH/$dO_2$ conditions. Running the bioreactors at a pH set point of 7.32 at either high or low oxygen has a marked impact on specific productivity. The pH 7.32 bioreactor run at high oxygen (50%) achieved a higher integrated viable cell concentration and a higher final titer as compared to its 5% $dO_2$ counterpart. The bioreactors run at pH 6.95±0.02 had a higher specific productivity and was similar in productivity to the 2 L bioreactors run under control conditions. Therefore, at pH 6.95, the $dO_2$ set point differential (5% vs. 50%) did not have as much of an impact on specific productivity or final titer as compared to impact of $dO_2$ at pH 7.32. The bioreactors run at control conditions of pH 7.0 and 15% $dO_2$ produced the highest cumulative integrated viable cell concentration. The bioreactors run at control conditions also out performed the bioreactor cell cultures run at pH 7.32 and 50% $dO_2$. The bioreactors run at control conditions produced eculizumab at 1600 mg/L, over 400 mg/L higher bioreactors run at the non-control conditions." and insert the same in Column 36, Line 24, as a continuation of the same paragraph.

In Column 37, Line 28, delete "began at 3 sl/hour and ramped up to 9 sl/hour" and insert -- began at 3 sL/hour and ramped up to 9 sL/hour --, therefor.

In Column 39, Line 26, delete "4≥protein" and insert -- 4>protein --, therefor.

In Column 40, Line 11, delete "new" and insert -- New --, therefor.

In the Claims

In Column 43, Line 59, in Claim 2, delete "the the" and insert -- the --, therefor.

In Column 44, Lines 60-61, in Claim 9, delete "between about between about" and insert -- between about --, therefor.